(12) United States Patent
Luo et al.

(10) Patent No.: US 10,494,635 B2
(45) Date of Patent: Dec. 3, 2019

(54) ANTEROGRADE MULTI-SYNAPTIC TRANSNEURONAL TRACER

(71) Applicant: WUHAN INSTITUTE OF VIROLOGY, CHINESE ACADEMY OF SCIENCES, Wuhan (CN)

(72) Inventors: Minhua Luo, Wuhan (CN); Wenbo Zeng, Wuhan (CN); Haifei Jiang, Wuhan (CN); Fei Zhao, Wuhan (CN); Hong Yang, Wuhan (CN); Yige Song, Wuhan (CN); Zhangzhou Shen, Wuhan (CN)

(73) Assignee: Wuhan Institute of Virology, CNS, Wuhan (CN)

( * ) Notice: Subject to any disclaimer, the term of this patent is extended or adjusted under 35 U.S.C. 154(b) by 2 days.

(21) Appl. No.: 15/747,742

(22) PCT Filed: Nov. 7, 2016

(86) PCT No.: PCT/CN2016/104880
§ 371 (c)(1),
(2) Date: Jan. 25, 2018

(87) PCT Pub. No.: WO2018/082091
PCT Pub. Date: May 11, 2018

(65) Prior Publication Data
US 2018/0371467 A1 Dec. 27, 2018

(51) Int. Cl.
| | |
|---|---|
| A01N 63/00 | (2006.01) |
| C12N 15/00 | (2006.01) |
| C07H 21/04 | (2006.01) |
| C12N 15/65 | (2006.01) |
| C12N 7/00 | (2006.01) |
| C12N 15/10 | (2006.01) |
| C12N 15/62 | (2006.01) |
| C12N 15/66 | (2006.01) |
| C12N 15/85 | (2006.01) |

(52) U.S. Cl.
CPC .............. *C12N 15/65* (2013.01); *C12N 7/00* (2013.01); *C12N 15/1041* (2013.01); *C12N 15/1065* (2013.01); *C12N 15/62* (2013.01); *C12N 15/66* (2013.01); *C12N 2015/859* (2013.01); *C12N 2710/16611* (2013.01); *C12N 2710/16632* (2013.01); *C12N 2710/16641* (2013.01); *C12N 2710/16671* (2013.01)

(58) Field of Classification Search
CPC .......... C12N 7/00; C12N 15/62; C12N 15/66; C12N 2710/16611; C12N 2710/16671; C07H 21/04
USPC ............. 424/93.2; 435/320.1; 536/23.7, 24.1
See application file for complete search history.

(56) References Cited

U.S. PATENT DOCUMENTS

2009/0208419 A1 * 8/2009 Gambhir et al.

OTHER PUBLICATIONS

Hogue et al., 2015, Viruses, vol. 7, p. 5933-5961.*
Guiliano et al., 2000, N_Geneseq Accession No. AAA27573, computer printout, pp. 5-7.*
Cepko et al., 2010, N_Geneseq Accession No. AYL12927, computer printout, pp. 15-17.*
Vainstein et al., 2009, N_Geneseq Accession No. AXT21040, computer printout, pp. 5-6.*
Ohmori et al., 2007, N_Geneseq Accession No. AEX82758, computer printout, pp. 16-19.*
Fan Y, et al. 2013. Genome of the Chinese tree shrew. Nat Commun 4:1426.
Li L, et al. 2015. Herpes Simplex Virus 1 Infection of Tree Shrews Differs from That of Mice in the Severity of Acute Infection and Viral . . . J Virol 90:790-804.
Park JW, et al. 2006. Microfluidic culture platform for neuroscience research. Nat Protoc 1:2128-2136.
Szpara ML, et al. 2010. Sequence variability in clinical and laboratory isolates of herpes simplex virus 1 reveals new mutations. J Virol 84:5303-5313.
Taylor AM, et al. 2005. A microfluidic culture platform for CNS axonal injury, regeneration and transport. Nature Methods 2:599-605.
Harris J, et al. 2007. Fabrication of a Microfluidic Device for the Compartmentalization of Neuron Soma and Axons. doi:doi:10.3791/261:e261.

(Continued)

*Primary Examiner* — Shin Lin Chen
(74) *Attorney, Agent, or Firm* — Guangzhou Yihe IP Service

(57) ABSTRACT

A recombinant Herpes Simplex Virus type 1 (HSV-1) strain H129-derived anterograde multi-synaptic transneuronal viral tracer for multi-synaptic neural circuit mapping comprises two or more fluorescence expression cassettes being integrated into the H129 genome at different locations; wherein each fluorescence expression cassette contains at least two copies of fluorescent protein-encoding sequence that are arranged in tandem, and at least one linker-encoding sequence, where at least one linker-encoding sequence is disposed between two fluorescent protein-encoding sequences, allowing transcription of fluorescent protein-encoding sequences and linker-encoding sequence as a single transcript; and wherein the linker-encoding sequence encodes a linker peptide containing at least two adjacent amino acids that are highly inefficient in forming a peptide bond between them; thereby, when the single transcript is translated, at least two fluorescent proteins are stoichiometrically generated due to the impedence of peptide bond formation by the linker peptide.

8 Claims, 24 Drawing Sheets

Specification includes a Sequence Listing.

(56) References Cited

OTHER PUBLICATIONS

Paxinos G, et al. 2003. The Mouse Brain in Stereotaxic Coordinates. Academic Press.
Zhou J-N, et al. 2017. The Tree Shrew (*Tupaia belangeri chinensis*) Brain in Stereotaxic Coordinates. Springer Singapore.
Xiong H, et al. 2014. Chemical reactivation of quenched fluorescent protein molecules enables resin-embedded fluorescence microimaging. Nat Commun 5:3992.
Zheng T, et al. 2013. Visualization of brain circuits using two-photon fluorescence micro-optical sectioning tomography. Opt Express 21:9839-9850.
Gong H, et al. 2013. Continuously tracing brain-wide long-distance axonal projections in mice at a one-micron voxel resolution. Neuroimage 74:87-98.
Quan T, et al. 2016. NeuroGPS-Tree: automatic reconstruction of large-scale neuronal populations with dense neurites. Nat Methods 13:51-54.
Kelly RM, et al. 2003. Cerebellar loops with motor cortex and prefrontal cortex of a nonhuman primate. J Neurosci 23:8432-8444.
Archin NM, et al. 2002. Rapid spread of a neurovirulent strain of HSV-1 through the CNS of BALB/c mice following anterior chamber inoculation. J Neurovirol 8:122-135.
Beier KT, et al. 2016. Anterograde or Retrograde Transsynaptic Circuit Tracing in Vertebrates with Vesicular Stomatitis Virus Vectors. Curr Protoc Neurosci 74:1 26 21-21 26 27.
McGovern AE, et al. 2012. Anterograde neuronal circuit tracing using a genetically modified herpes simplex virus expressing EGFP. J Neurosci Methods 209:158-167.
Wadsworth S, et al. 1975. Anatomy of herpes simplex virus DNA. II. Size, composition, and arrangement of inverted terminal repetitions. J Virol 15:1487-1497.
Delius H, et al. 1976. A partial denaturation map of herpes simplex virus type 1 DNA: evidence for inversions of the unique DNA regions. J Gen Virol 33:125-133.
He B, et al. 1997. Suppression of the phenotype of gamma(1)34. 5—herpes simplex virus 1: failure of activated RNA-dependent . . . J Virol 71:6049-6054.
Wagner M, et al. 1999. Systematic excision of vector sequences from the BAC-cloned herpesvirus genome during virus reconstitution. J Virol 73:7056-7060.
Messerle M, et al. 1997. Cloning and mutagenesis of a herpesvirus genome as an infectious bacterial artificial chromosome. Proc Natl Acad Sci U S A 94:14759-14763.
Seibenhener ML, et al. 2012. Isolation and culture of hippocampal neurons from prenatal mice. J Vis Exp doi:10.3791/3634.
Nassi JJ, et al. 2015. Neuroanatomy goes viral! Front Neuroanat 9:80.
Beier KT, et al. 2013. Vesicular stomatitis virus with the rabies virus glycoprotein directs retrograde transsynaptic transport . . . Front Neural Circuits 7:11.
Beier KT, et al. 2011. Anterograde or retrograde transsynaptic labeling of CNS neurons with vesicular stomatitis virus vectors. Proc Natl Acad Sci U S A 108:15414-15419.
McGovern AE, et al. 2015. Distinct brainstem and forebrain circuits receiving tracheal sensory neuron inputs revealed . . . J Neurosci 35:7041-7055.
Lo L, et al. 2011. A Cre-dependent, anterograde transsynaptic viral tracer for mapping output pathways of genetically marked neurons. Neuron 72:938-950.
Zemanick MC, et al. 1991. Direction of transneuronal transport of herpes simplex virus 1 in the primate motor system . . . Proc Natl Acad Sci U S A 88:8048-8051.
Lavail JH, et al. 1997. Factors that contribute to the transneuronal spread of herpes simplex virus. J Neurosci Res 49:485-496.
Sun N, et al. 1996. Anterograde, transneuronal transport of herpes simplex virus type 1 strain H129 in the murine visual system. J Virol 70:5405-5413.
Barnett EM, et al. 1995. Anterograde tracing of trigeminal afferent pathways from the murine tooth pulp to cortex using herpes simplex virus type 1. J Neurosci 15:2972-2984.
Rinaman L, et al. 2004. Anterograde transneuronal viral tracing of central viscerosensory pathways in rats. Journal of Neuroscience 24:2782-2786.

* cited by examiner (e)

(f)

(c)

(d)

(e)

(a)

(b)

(c)

(d)

(a)

ANTEROGRADE MULTI-SYNAPTIC TRANSNEURONAL TRACER

FIELD OF THE INVENTION

The present invention generally relates to neural biology, and more particularly to an anterograde multi-synaptic transneuronal viral tracer.

BACKGROUND OF THE INVENTION

Mapping brain connectome is essential for understanding how the brain works. As the basic unit of neural function, neural circuit serves as the bridge between macroscale structure/function and microscale molecules/signal pathways. However, the structure for many specific functional neural circuits, including the components, connections and distributions, remains to be elucidated. New tracing technology and tracers, especially viral tracers, have contributed to discovery of novel circuits and revealing new features of known canonical circuits.

Viral tracers have been used in neuroscience research. Viral tracers derived from rabies virus (RV) and pseudorabies virus (PRV) have the capacity of tracing neural circuits to retrogradely map the input neural networks [1]. Recombinant vesicular stomatitis virus (VSV) has also been used for anterograde or retrograde transsynaptic circuit tracing [2, 3]. Human herpes simplex virus type 1 (HSV-1) strain H129 (H129) is a potential anterograde transsynaptic neural circuit tracer [4, 5].

However, mapping the details of the output neural circuit anterogradely with high efficiency and resolution remains a challenge. Therefore, there is an imperative need to develop an anterograde tracer with high transsynaptic labelling efficiency.

SUMMARY OF THE INVENTION

The present invention provides a recombinant Herpes Simplex Virus type 1 (HSV-1) strain H129-derived anterograde multi-synaptic transneuronal viral tracer for multi-synaptic neural circuit mapping. In one embodiment, the recombinant H129-derived anterograde multi-synaptic transneuronal viral tracer comprises two or more fluorescence expression cassettes being integrated into the H129 genome at different locations; wherein each fluorescence expression cassette contains at least two copies of fluorescent protein-encoding sequence that are arranged in tandem, and at least one linker-encoding sequence, where at least one linker-encoding sequence is disposed between two fluorescent protein-encoding sequences, allowing transcription of fluorescent protein-encoding sequences and linker-encoding sequence as a single transcript; and wherein the linker-encoding sequence encodes a linker peptide containing at least two adjacent amino acids that are highly inefficient in forming a peptide bond between them; thereby, when the single transcript is translated, at least two fluorescent proteins are stoichiometrically generated due to the impedance of peptide bond formation by the linker peptide.

In another embodiment of the recombinant H129-derived anterograde multi-synaptic transneuronal viral tracer, the fluorescence expression cassette further comprises a promoter, wherein the promoter controls transcription of the fluorescent protein-encoding sequence and linker-encoding sequence.

In another embodiment of the recombinant H129-derived anterograde multi-synaptic transneuronal viral tracer, the promoter is operable in neuronal cells and selected from the group consisting of CMV promoter, SV40 promoter, CAG promoter, EF1a promoter, TH promoter, and Syn1 promoter.

In another embodiment of the recombinant H129-derived anterograde multi-synaptic transneuronal viral tracer, the fluorescent protein-encoding sequence in one fluorescence expression cassette encodes the same or different fluorescent proteins.

In another embodiment of the recombinant H129-derived anterograde multi-synaptic transneuronal viral tracer, the fluorescent protein-encoding sequence encodes a green fluorescence protein (GFP) represented by an amino acid sequence (SEQ ID NO 2) or a variant thereof.

In another embodiment of the recombinant H129-derived anterograde multi-synaptic transneuronal viral tracer, the fluorescent protein-encoding sequence encodes a membrane-bound green fluorescence protein (mGFP) represented by an amino acid sequence (SEQ ID NO 4) or a variant thereof.

In another embodiment of the recombinant H129-derived anterograde multi-synaptic transneuronal viral tracer, the at least two adjacent amino acids of the linker peptide are glycine and proline.

In another embodiment of the recombinant H129-derived anterograde multi-synaptic transneuronal viral tracer, the linker-encoding sequence encodes a peptide represented by an amino acid sequence (SEQ ID NO 6) or a variant thereof.

In another embodiment of the recombinant H129-derived anterograde multi-synaptic transneuronal viral tracer, the fluorescent protein-encoding sequence and linker-encoding sequence encode a peptide represented by an amino acid sequence (SEQ ID NO 8) or variant thereof.

In another embodiment, the recombinant H129-derived anterograde multi-synaptic transneuronal viral tracer further comprises a BAC sequence.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the Figures, in which like reference numerals denote like elements.

DETAILED DESCRIPTION OF THE INVENTION

Figure 1:
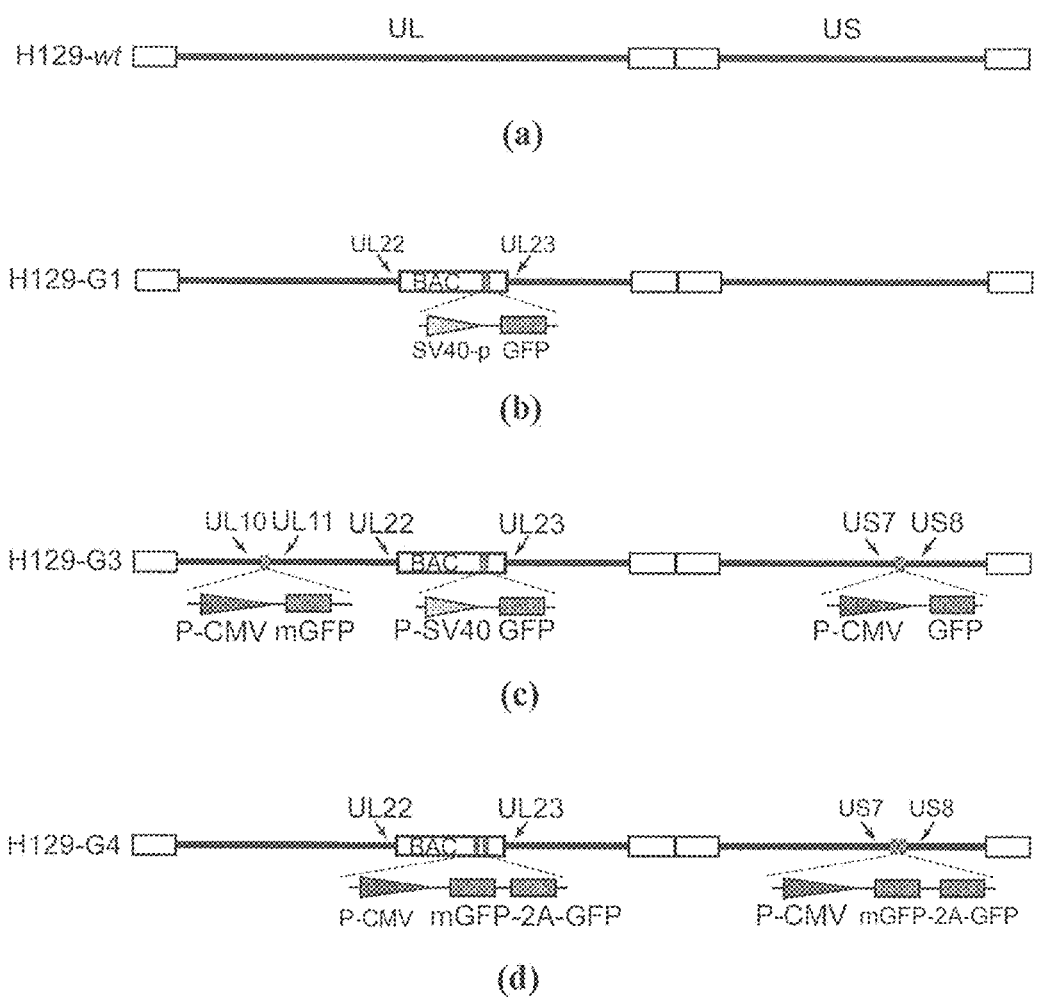
FIG. 1 shows the schematic diagrams of (a) the genome structure of H129-wt, (b) the genome structure of H129-G1, (c) the genome structure of H129-G3, (d) the genome structure of H129-G4, (e) construction of pUS-F6, and (f) construction of H129-BAC (i.e. H129-G1).
Figure 1:
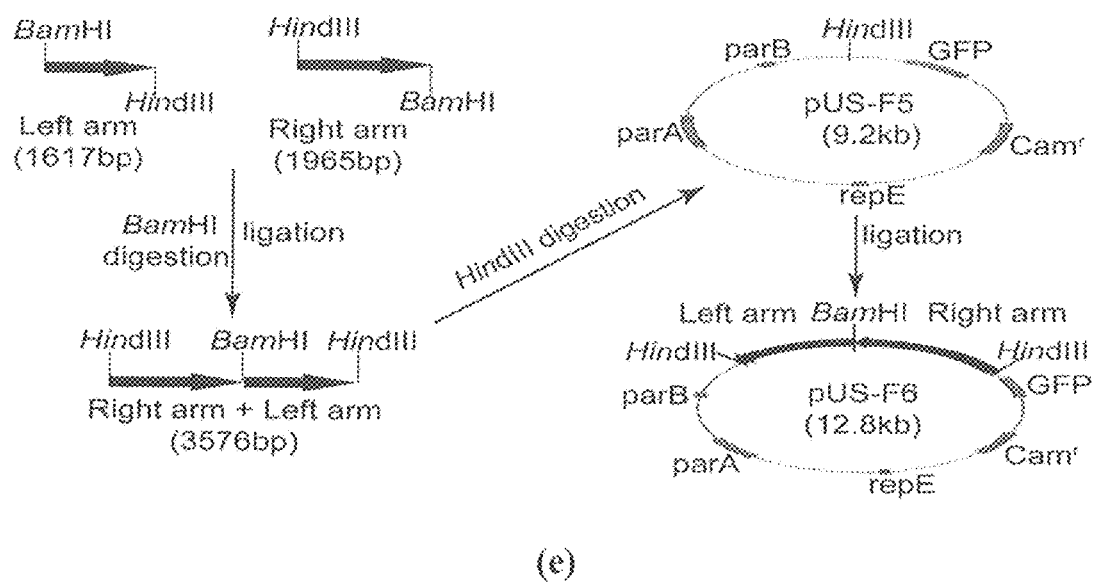
Figure 1:
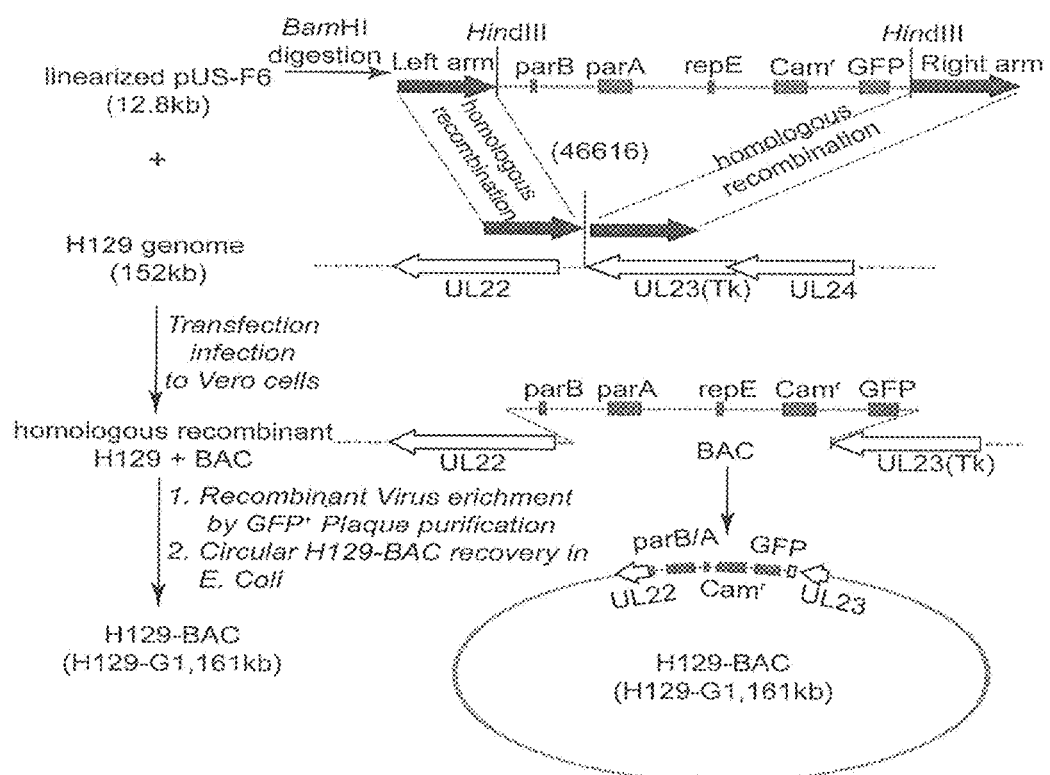

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, for example, *Molecular Cloning: A Laboratory Manual*, second edition (Sambrook et al., 1989); *Current Protocols in Molecular Biology* (F. M. Ausubel et al., eds., 1987).

Herpes Simplex Virus type 1 (HSV-1) is a ubiquitous and opportunistic pathogen. The naturally neuronal tropism and transneuronal transmitting capacity make this virus a potential neuronal circuit tracer.

HSV-1 strain McIntyre-B spreads retrogradely, whereas HSV-1 strain H129 prefers anterograde transneuronal transport [6-8]. Multiple studies have applied this virus in various pathways and different animal models [6, 9-12]. In particular, the development of genetically modified fluorescent protein (FP)-expressing H129 prompted the investigations of this virus strain in anterograde neuronal circuit tracing [3, 13]. However, due to limited labeling intensity, those H129-derived tracers allow neither the visualization of projecting paths, nor the display of neuron morphology in detail [5, 14].

The present invention provides a H129-derived anterograde multi-synaptic transneuronal viral tracer for mapping multi-synaptic neural circuits, where the H129-derived anterograde multi-synaptic transneuronal viral tracer has high labeling intensity sufficient for visualizing fine neuronal structures including axonal fibers and dendritic spines and is also compatible with fluorescence Micro-Optical Sectioning Tomography (fMOST). Briefly, the H129-derived anterograde multi-synaptic transneuronal viral tracer is a recombinant Herpes Simplex Virus type 1 (HSV-1) strain H129 that comprises two or more fluorescence expression cassettes being integrated into the H129 genome at different locations, wherein each fluorescence expression cassette contains at least two copies of fluorescent protein-encoding sequence that are arranged in tandem, and at least one linker-encoding sequence, where at least one linker-encoding sequence is disposed between two fluorescent protein-encoding sequences, allowing transcription of fluorescent protein-encoding sequences and linker-encoding sequence as a single transcript; and wherein the linker-encoding sequence encodes a linker peptide containing at least two adjacent amino acids that are highly inefficient in forming a peptide bond between them; thereby, when the single transcript is translated, at least two fluorescent proteins are stoichiometrically generated due to the impedence of peptide bond formation by the linker peptide. For example, when two fluorescent protein-encoding sequences coupled by the linker-encoding sequence are translated, two fluorescence proteins (not as one fused protein) are stoichiometrically produced.

In certain embodiments, Herpes Simplex Virus type 1 (HSV-1) strain H129 has a large genome (GenBank GU734772.1). As shown in FIG. 1(a), H129-wt has a typical HSV-1 structural architecture. The HSV-1 genome can be viewed as consisting of two covalently linked components, designated as unique long (L) and unique short (S). Each component consists of unique sequences bracketed by inverted repeats. The L and S components of HSV-1 are found inverted relative to one another, to yield four linear isomers.

In certain embodiments, the fluorescence expression cassette comprises a promoter, at least two copies of fluorescent protein-encoding sequence that are arranged in tandem, and at least one linker-encoding sequence, where at least one linker-encoding sequence is disposed between two fluorescent protein-encoding sequences so that the fluorescent protein-encoding sequences and linker-encoding sequences are transcribed as a single transcript.

In certain embodiments, the promoter can be any promoter operable in neuronal cells. In certain embodiments, the promoter includes CMV promoter, SV40 promoter, CAG promoter, EF1a promoter, TH promoter, and Syn1 promoter.

In certain embodiments, the fluorescent protein-encoding sequence suitable for the present invention can be any fluorescence genes available in the field in the present and future. The fluorescence genes can be wild-type or recombinant derivatives as long as they have no less fluorescent intensity. For example, the fluorescent protein-encoding genes include GFP (green fluorescent protein), eGFP (enhanced green fluorescent protein), mGFP (membrane bound form of EGFP), sfGFP (superfolder green fluorescent protein), EYFP (enhanced yellow fluorescent protein), ECFP (enhanced cyan fluorescent protein), EBFP2 (enhanced blue fluorescent protein 2), tdTomato, MRFP (monomer red fluorescent protein, mCherry, Ypet, mKO, mkate, etc. In certain embodiments, the at least two fluorescent protein-encoding sequence in one expression cassette can be the same or different. In certain embodiments, the fluorescent protein-encoding sequence is represented by a nucleotide sequence (SEQ ID NO 1) encoding a green fluorescence protein (GFP) represented by an amino acid sequence (SEQ ID NO 2). In certain embodiments, the fluorescent-encoding construct is represented by a nucleotide sequence (SEQ ID NO 3) encoding a membrane-bound green fluorescence protein (mGFP) represented by an amino acid sequence (SEQ ID NO 4). In certain embodiments, their variants can be used; where the "variant" is defined as a protein that shares at least 90%, preferably 95%, more preferably 98% or even more preferably 99% identity with an amino acid sequence represented by a SEQ ID NO number as long as the changes in the variant do not interfere its function.

In certain embodiments, the linker-encoding sequence encodes a linker peptide, where the linker peptide contains at least two adjacent amino acids that are highly inefficient in forming a peptide bond between them. In certain embodiments, the at least two adjacent amino acids are glycine and proline. In certain embodiments, the linker-encoding sequence represented by a nucleotide sequence (SEQ ID NO 5) encodes a linker peptide represented by an amino acid sequence (SEQ ID NO 6). In certain embodiments, their variants can be used; where the "variant" is defined as a protein that shares at least 90%, preferably 95%, more preferably 98% or even more preferably 99% identity with an amino acid sequence represented by a SEQ ID NO number as long as the changes in the variant do not interfere its function.

In certain embodiments, the at least two copies of fluorescent protein-encoding sequence and at least one linker sequence are represented by a nucleotide sequence (SEQ ID NO 7) encoding a polypeptide represented by an amino acid sequence (SEQ ID NO 8). In certain embodiments, their variants can be used; where the "variant" is defined as a polypeptide that shares at least 90%, preferably 95%, more preferably 98% or even more preferably 99% identity with an amino acid sequence represented by a SEQ ID NO number as long as the changes in the variant do not interfere its function.

In certain embodiments, the fluorescence expression cassettes are inserted into any site of H129 genome as long as the insertion does not interfere with viral replication. In certain embodiments, the insertion site is located at the noncoding region of any two adjacent genes. In certain embodiments, the insertion site of BAC is 46616-46617, and in H129-G3, mGFP was inserted at 24671-24672.

In certain embodiments, the recombinant H129 genome contains a bacterial artificial chromosome (BAC) sequence; thereby the recombinant H129 genome can be manipulated in bacteria. The BAC sequence can be inserted into any appropriate site of H129 genome; for example, the BAC sequence is inserted at 46616-46617 of the viral genome. The large viral genome can be maintained in the BAC, facilitating genetical manipulation, such as insertion or deletion of one or more genes by homologous recombination, and subsequent transfection into eukaryotic cells to rescue infectious virus with the target gene deleted or added [18, 19].

The following examples are provided for the purpose of illustrating the application of the principles of the present invention; they are by no means intended to be the coverage of the present invention.

EXAMPLES (1) Cells and Cell Culture

VERO-E6 cells (VERO, ATCC#CRL-1586) were cultured in Dulbecco's modified Eagle medium (DMEM) containing 10% fetal bovine serum (FBS) and penicillin-streptomycin (100 U/ml of penicillin and 100 μg/ml of streptomycin, Gibco/Life Technology).

Fetal mouse hippocampal neurons were isolated and cultured following the established protocol [20, 21]. Briefly, hippocampi were dissected from C57BL/6 mouse pups at embryonic day 18.5 (E18.5), sliced and further dissociated with trypsin/DNase I for 15 min at 37° C. Isolated neurons were washed with sterile Hank's Balance Salt Solution (HBSS), resuspended and cultured in neurobasal medium supplemented with 2% B27, GlutaMAX (25 μM) and penicillin-streptomycin (100 U/ml and 100 μg/ml). Medium was changed every other day.

(2) Construction of H129-G1

H129-BAC (i.e. H129-G1) was constructed by cloning the genome of H129 (GenBank GU734772.1) into a BAC containing a GFP. FIGS. 1e and 1f show the process of constructing H129-G1.

(2.1) Preparation of H129-wt Viral Genomic DNA

Wild type H129 virus [22] was used to infect VERO cells at an MOI of 1. At 12 h post-infection, cells were scraped and collected by centrifugation. The collected cells were washed once with solution I (10 mM Tris, 10 mM EDTA, pH 8.0), then resuspended in 0.5 ml solution I containing 0.25 mg of proteinase K/ml (Roche), 0.6% sodium dodecyl sulfate (SDS) (Sinopharm Group, China), and 1 M sodium chloride, and incubated at 50° C. for 2 hours, then added RNase I (TaKaRa, Japan) to a final concentration of 10 mg/ml and incubated at 37° C. for 1 hour, and finally extracted the cells using phenol chloroform (1:1) to obtain DNA precipitation. The DNA precipitation was dried, and then resuspended in sterile de-ionized water (100 μl). This dissolved DNA solution contains a large amount of H129-wt genomic DNA.

(2.2) PCR Amplification of Left and Right Homologous Arms Respectively

H129-wt virus genome was used as template for PCR amplification of left and right homologous arms. The left arm (L-arm) consisted of 1606 bp corresponding to genome sequence of No. 45011-46616 in HSV-1-H129 genome (GenBank accession number: GU734772.1); the right arm (R-arm) consisted of 1954 bp corresponding to genome sequence of No. 46617-48570. The total volume of the PCR reaction system (Primestar DNA polymerase, Takara) was 50 μl, consisting of 10 μl 5× buffer, 4 μl dNTP, 1.5 μl forward primer, 1.5 μl reverse primer, 0.5 μl Primestar enzyme, 1 μl template, and 31.5 μl $H_2O$. Left arm forward primer sequence was 5'-cgggatccagactgacacattaaaaaacac-3' (SEQ ID NO 9), left arm reverse primer sequence was 5'-cccaagct-tataacttcgtataatgtatgctatagacgttataacggaaggagacaataccg-3' (SEQ ID NO 10), right arm forward primer sequence was 5'-cccaagcttataacttcgtataatgtatgctatacgaagttattcagttagcctc-ccccatctc-3' (SEQ ID NO 11), and right arm reverse primer sequence was 5'-cgggatcccttcggacctcgcggggggccgc-3' (SEQ ID NO 12). The amplification conditions were as follows: 1) 94° C. 2 min; 2) 98° C. 15 s; 3) 55° C. 15 s; 4) 72° C. 2 min; 5) 72° C. 10 min; 6) 16° C. 10 min; where steps 2-4 were cycled 30 times. Then the PCR product was run on 1% agarose gel electrophoresis (Biowest, Spain), and left and right arms for homologous recombination were purified following the instructions from the kit (Omega, US).

(2.3) Ligation of Left and Right Homologous Arms

The purified left and right arms were digested respectively by restriction endonuclease BamHI (TaKaRa); the total volume of enzyme reaction was 50 μl, and DNA was 2 μg; incubation was about 4 hours at 37° C. in water bath; digested DNAs were purified by 1% agarose gel electrophoresis. The purified left and right homologous arms were directly ligated, where the reaction volume of ligation was 10 μl, consisting of 1 μl T4 DNA Ligase (TaKaRa), 1 μl 10× buffer, 8 μl left and right arm DNAs (concentration ratio 1:1). After incubation of 4 hours at 16° C., the full length of left and right arms (L+R) was amplified by PCR, where the total volume of PCR amplification was 50 μl, consisting of 10 μl 5× buffer, 4 μl dNTP, 1.5 μl left arm forward primer (5'-cgggatccagactgacacattaaaaaacac-3' SEQ ID NO 13), 1.5 μl right arm reverse primer (5'-cgggatcccttcggac-ctcgcggggggccgc-3' SEQ ID NO 14), 0.5 μl PrimeStar enzyme, 1 μl template, 31.5 μl $H_2O$. The amplification conditions were as follows: 1) 94° C. 2 min; 2) 98° C. 15 s; 3) 55° C. 15 s; 4) 72° C. 2 min; 5) 72° C. 10 min; 6) 16° C. 10 min; steps 2-4 cycled 30 times. Full length (L+R) DNA fragment of homologous recombination arm was purified by 1% agarose gel electrophoresis.

(2.4) Construction of pUS-F6

Cyclic pUS-F5 vector (SEQ ID NO 59) and above purified L+R DNA fragments were digested by HindIII (TaKaRa), respectively. The total volume of enzyme digestion was 50 μl containing 2 μg DNA; after incubated at 37° C. in water bath for about 4 hours, they were purified by 1% agarose gel electrophoresis respectively. The purified linear pUS-F5 vector and L+R DNA fragments were ligated in ligation reaction. The total volume of ligation reaction was 10 μl, consisting of 1 μl T4 DNA Ligase (TaKaRa), 1 μl 10× buffer, 4 μl μl L+R DNA fragments and 4 μl linear pUS-F5 vector. After incubation at 16° C. for about 4 hours, the reaction mixture was directly transfected into activated *E. coli* DH5α cells; cultured at 37° C. overnight; by PCR verification and sequencing, the pUS-F5 plasmid containing the left and right arm homologous sequence was designated as pUS-F6.

(2.5) Linearization of pUS-F6 pUS-F6 plasmid was extracted using Plasmid Extraction Kit (Promega, US); the extracted cyclic pUS-F6 plasmid was digested with BamHI, where the total volume of enzyme reaction was 50 μl containing 2 μg DNA; setting up 4 parallel digestion tubes; after incubation at 37° C. in water bath for 4 hours, directly added into each tube 2 times of anhydrous alcohol and 20 μl sodium acetate (3M); after mixing, incubated at −80° C. for about 10 minutes; resuspended DNA precipitate in a small amount of sterile de-ionized water (20 μl), and the concentration was finally determined using NanoDrop 2000 (Thermo Scientific).

(2.6) Transfection of Linearized pUS-F6 Plasmids into 293T Cells

Cells were plated in 6-well plate the day before transfection and incubated overnight; cell confluence reached 50-80% at the day of transfection. 2 μg linear pUS-F6 plasmid DNA was mixed with DMEM medium containing no serum and antibiotics (GIBCO, US), then added 10 μl transfection reagent (SuperFect Transfection Reagent, Qiagen GmbH), and incubated at room temperature for 10-15 minutes; then added the transfection mixture into 6-well plate, and cultured for 3 to 4 hours; then washed once with PBS, added complete DMEM medium (GIBCO), and cultured in $CO_2$ incubator at 37° C.

(2.7) Infection of H129-wt Virus 5-6 hours after the plasmid transfection in above step of (2.6), 293T cells were infected with H129-wt virus at multiplicity of infection (MOI) of 1-3 (MOI=1-3), and immediately put into 5% $CO_2$ incubator (Thermo Scientific) and cultured at 37° C.

(2.8) Cell Sorting by FACS 24 hours after the virus infection in the above step (2.7), the expression of green fluorescent protein was observed under an inverted fluorescence microscope (Nikon, Japan). If the positive rate is higher than 1%, they are ready for cell sorting 293T cells were first treated by trypsin (GIBCO) and washed by PBS once; then cell suspensions were filtered by 300 mesh membrane treated with sterilization, sorting the 293T cells passing through the 300 mesh membrane by FACS. GFP expression positive 293T cells were individually sorted out, and co-cultured with prior plated VERO cells.

(2.9) Preparation of H129-G1 Recombination Viral Genomic DNA

After the sorted GFP positive 293T cells and VERO cells were co-cultured in above step (2.8) for about 48 hours, the expression of green fluorescent protein (GFP) was observed. If the GFP positive rate is more than 20%, H129-G1 recombination viral genomic DNA could be prepared by the same method as described in above step (2.1).

Figure 2:
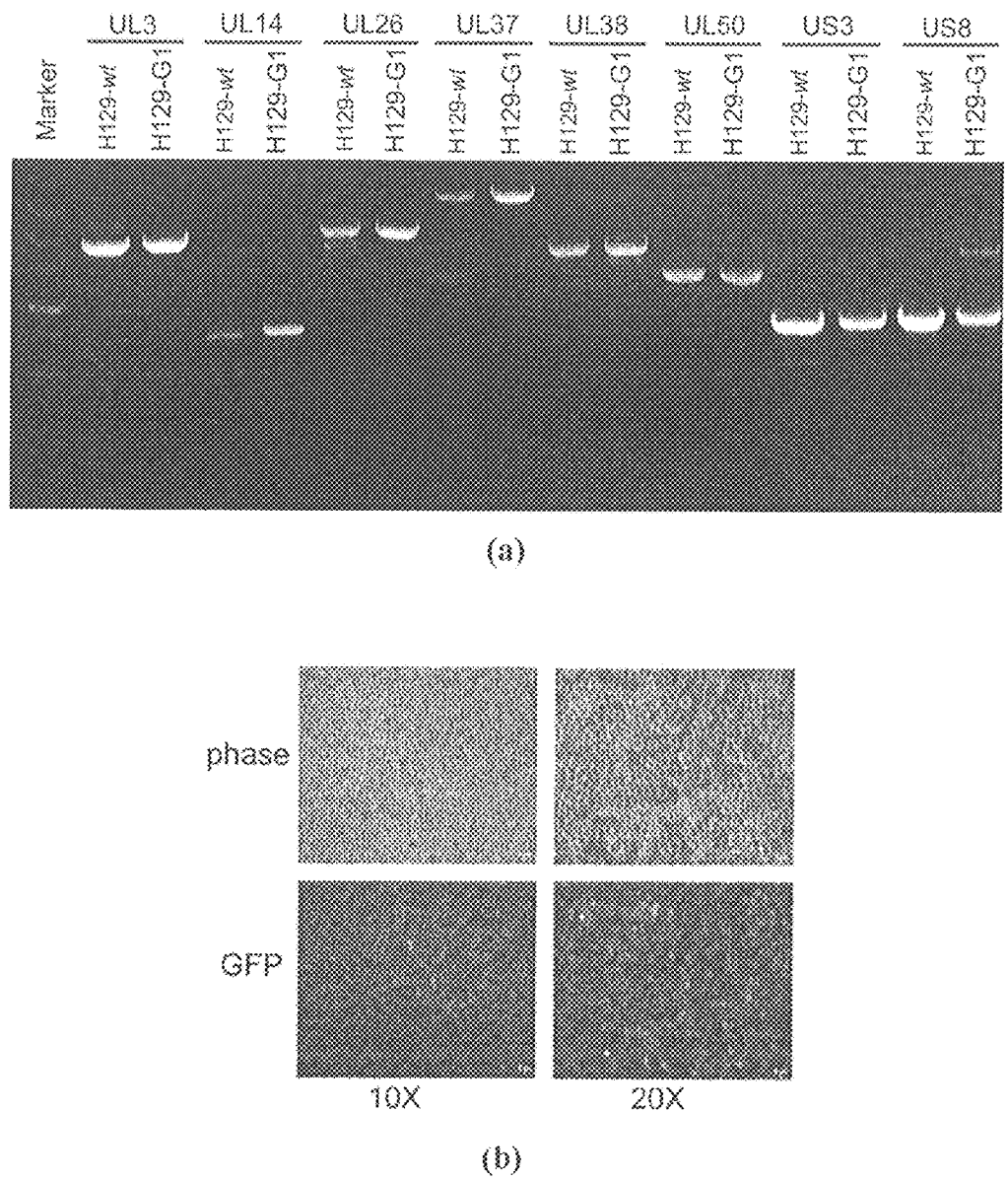
FIG. 2 presents: (a) identification results of H129-G1 monoclones by PCR; (b) GFP signal from the expression of GFP accompanying virus replication and resulted cytopathic effects; (c) viral proteins by Western blot; (d) the growth curves of H129-wt and H129-G1; (e) the growth curves of H129-wt, H129-G1, H129-G3 and H129-G4 in VERO cells.
Figure 2:
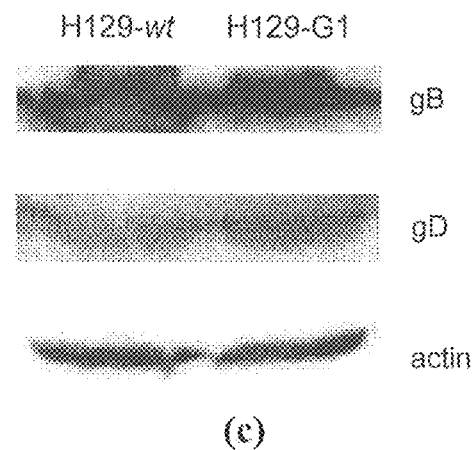
Figure 2:
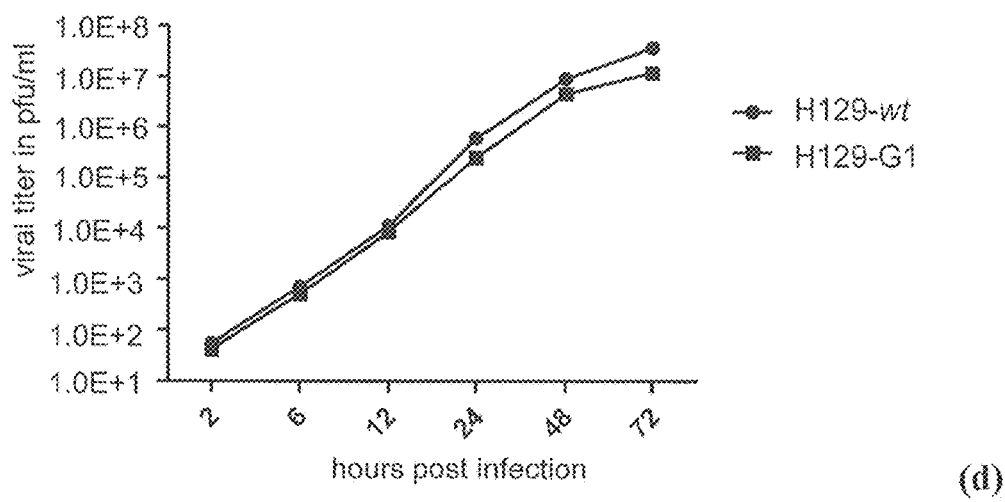
Figure 2:
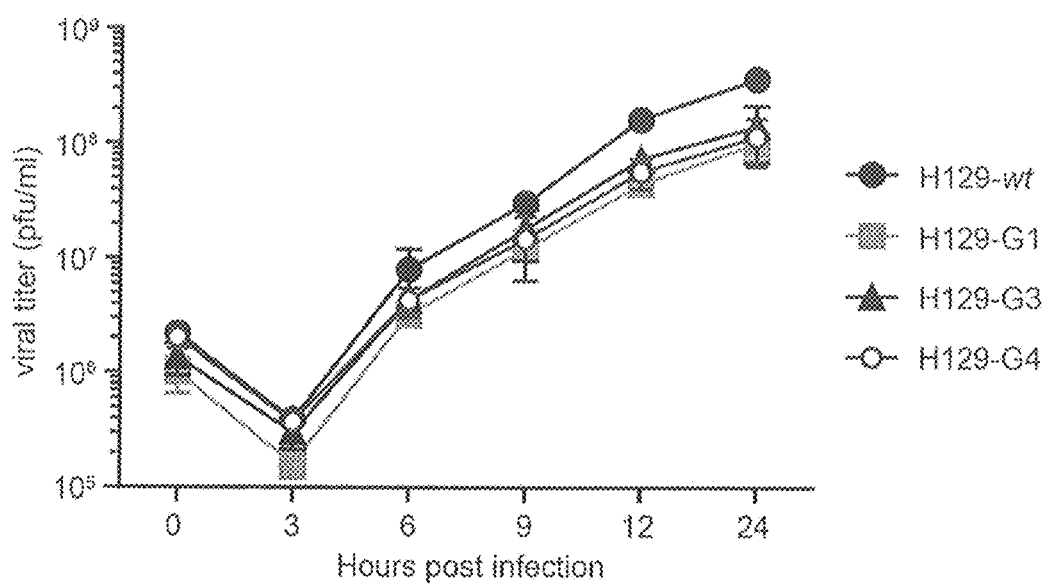

(2.10) Preliminary Screening and Verification of Individual H129-G1 Infectious Clones H129-G1 recombinant viral genomic DNA prepared in the above step (2.9) was electroporated (1.6 KV, 25 uF and 200 Ω, 1 mm) into activated DH10B cells (Invitrogen, US); DH10B cells were coated onto LB plates containing chloramphenicol (Kermel), and incubated at 37° C. culture for 36-48 hours. Monoclones were verified by PCR as described in the above steps (2.2). The verification sequences are H129-wt genes, including UL3, UL14, UL26, UL37, UL38, UL50, US3, US8 and US12. The following primers are included: UL3-F:TCGGTTTGAAAGGCATCG (SEQ ID NO 15), UL3-R: GACAAGGTCGCCATCTGCT (SEQ ID NO 16); UL14-F: GGGCACGCGAGACTATCA-GAG (SEQ ID NO 17), UL14-R: TCATTCGC-CATCGGGATAGTC (SEQ ID NO 18); UL26-F: ATGGAG-GAGCCCCTACCAGA (SEQ ID NO 19), UL26-R: TACCAAAGACCGGGGCGAAT (SEQ ID NO 20); UL37-F: TGGTAACTAGTTAACGGCAAGTCCG (SEQ ID NO 21), UL37-R: ATGCCGGGACTTAAGTGGCCGTATA (SEQ ID NO 22); UL38-F: ATGAAGACCAATCCGCTAC-CCGCA (SEQ ID NO 23), UL38-R: AACACTCGCGTTTCGGGTTTCAGT (SEQ ID NO 24); UL50-F: ATGAGTGGGGGATCCGG (SEQ ID NO 25). UL50-R: CCCGGAACGAACCCCAAGCT (SEQ ID NO 26); US3-F: GCCAACGACCACATCCCT (SEQ ID NO 27), US3 R: CAGCGGCAAACAAAGCAG (SEQ ID NO 28); US8-F: GGGGTITCTTCTCGGTGTTTG (SEQ ID NO 29), US8-R: GCGGTGCTGATGOTAATGTG (SEQ ID NO 30); US12-F: AAATGCCCTAGCACAGGGG (SEQ ID NO 31), US12-R: GGTCTCTCCGGCGCACATAA (SEQ ID NO 32). Using H129-wt as positive control, the verification results are shown in FIG. 2(a).

(2.11) Rescue Infectious Virus from H129-G1

The day before transfection, VERO cells were seeded onto 6-well plates until about 100% confluence. VERO cells were transfected with H129-G1 DNA obtained from the above step (2.10). Transfection mixtures were prepared as follows: 2 μg cyclic H129-G1 DNA, 10 μl SuperFect Transfection Reagent, and serum- and antibiotic-free DMEM culture media were mixed into 100 μl mixture, placed at room temperature for 5-10 minutes, then diluted with 600 μl serum- and antibiotics-free DMEM diluted to form the transfection mixture. The cell culture medium was removed; the cells were washed with pre-warmed PBS, then added the transfection mixture, and cultured in incubator. After 2-3 hours, the transfection mixture was sucked off; cells were washed once with PBS, and finally added DMEM medium for further culture. Cytopathic effects appeared about 48 hours after transfection with H129-G1 DNA. When observed under inverted microscope, cytopathic effects were observed, demonstrating that infectious virus was successfully rescued from H129-G1 DNA, as shown in FIG. 2(b). And then continuing the culture until all cells were cytopathic, the supernatant from the culture was collected, that contains H129-G1 recombinant virus, adding 1% of the DMSO for storage at −80° C.

(2.12) Detection of Protein Expressions of Recombinant Viruses

VERO cells were cultured in 100 mm culture dish at 37° C., 5% $CO_2$. After completely attached, the cells were infected at an MOI=1 by H129-wt and H129-G1, respectively. After adsorption at 37° C., 5% $CO_2$ culture incubator for 2 h, the inoculation solutions were replaced by MEM culture media containing 2% fetal bovine serum. After infection for 24 hours, cells were treated by trypsin, and collected by 1000 rmp centrifugation for 5 minutes. The cells were washed with pre-cooling PBS, and the supernatant was removed by centrifugation. The cells were collected and deposited in liquid nitrogen for 10 seconds, and were used as a sample for Western blot analysis.

Western blot was performed as follows: cell precipitates were added with 50 μl lysis buffer, and then sonicated. The protein contents were measured; then 5× sample buffer was added; same amount of protein samples (20 μg) were separated by SDS-polyacrylamide gel electrophoresis (PAGE). Subsequently membrane transfer was performed; first the nylon membrane was treated by methanol for 2 minutes, then immersed in the transfer buffer for 15 minutes, and proteins from PAGE were transferred to the membrane. Transfer conditions were constant current 200 mA, 90 minutes (Bio-Red, US). After the transfer was completed, the membrane was immediately washed with TBST solution for 3 minutes, then blocked with 5% milk/TBST for 1 hour, washed three times with TBST, and incubated with gD- and gB-specific monoclonal antibodies (Abcam) respectively. After washing, the membrane was incubated secondary antibodies and then washed again. Finally, the membrane was developed with chemical luminescence (Alpha Company, US); the results are shown in FIG. 2(c).

(2.13) Comparison of Growth Between H129-wt Virus and Recombinant H129-G1 Virus

VERO cells were passaged to 6-well plate (CORNING, US) with 60-80% confluence. When cells were completely attached, the cells were infected by H129-wt or H129-G1 respectively at 0.1 MOI (designated as 0 hour post-infection). The culture media were replaced after 2 hours. DMEM was used to culture the cells after infection, and then at 2, 6, 12, 24, 36, and 48 h samples were collected and stored at −80° C. When all virus samples were collected the virus titers of each sample were determined according to the following steps.

Virus titer was determined as follows: VERO cells were passaged to 12-well plate until they were 100% confluence. H129-wt and H129-G1 virus were serially diluted by culture media, and each concentration had three repeats. Culture media was siphoned off and cells were washed once with PBS. Each well was added 200 μl virus solution. After incubation for 1.5 hours, the virus inoculum was siphoned off, and the cells were washed three times with PBS. Each well was added 2 ml complete media containing 2% FBS, and the cells were cultured for 24 to 48 hours, and closely monitored until the plaque number at the minimum concentration no longer increased. The culture media were discarded, and each well was added with 300 μl of staining agent. After incubation, washed with double distilled water repeatedly, then counted plaque numbers and calculated the virus titers; the results are shown in FIG. 2(d).

(3) Construction of H129-G3

H129-G3 was derived from H129-G1 by homologous recombination. FIG. 1(c) shows structural architecture of H129-G3.

(3.1) Cassette Construction

By PCR, enzyme digestion, ligation and transformation, zeo$^R$ was cloned into the vector pRK-GFP (SEQ ID NO 60), and a cassette CMV promoter-GFP-ZeoR was constructed, where forward primer F: CGGGATCCCAAGTTTCGAG-GTCGAGTGTC (SEQ ID NO 33), reverse primer R: GCGAATTCGGAACGGACCGTGTTGACAA (SEQ ID NO 34). Using the same method, the mGFP was cloned into the vector pRK-kan, and a cassette CMV promoter-mGFP-kan$^R$ was constructed, where forward primer F: GCGTC-GACATGCTGTGCTGTATGAGAAG (SEQ ID NO 35), reverse primer R: CGGGATCCTTACTTGTACA-GCTCGTCC (SEQ ID NO 36).

(3.2) Preparation of E. coli Competent Cells Containing H129-G1

(i) E. coli DY380 containing H129-G1 cells were streaked on solid LB plate containing the corresponding resistance, cultured at 32° C. overnight;

(ii) Monoclones were picked up and cultured in 5 ml LB media, on a shaker at 32° C. overnight;

(iii) with a scale of 1:100 the culture media from (ii) was transferred to 100 ml culture medium, on a shaker, cultured at 32° C. about 3 hours till OD600 value is about 0.4-0.6 (0.55-0.6 for the best);

(iv) treated in water bath at 42° C. for 15 minutes;

(v) cooled the bacterial suspension on ice for about 10 minutes;

(vi) centrifuged at 4000 rpm at 4° C. for 10 minutes to remove supernatant;

(vii) resuspended bacteria precipitation in ultra pure water, and centrifuged at 4000 rpm at 4° C. for 10 minutes to remove supernatant;

(viii) resuspended bacteria precipitation with 10% glycerol, and centrifuged at 4000 rpm at 4° C. for 10 minutes to remove supernatant;

(x) repeat step (viii) once;

(x) resuspended bacteria precipitation in 800 μl pure water containing 10% of glycerol, aliquot 80 μl per tube, snap freezing in liquid nitrogen, stored at −80° C.

(3.3) PCR Amplification of Cassettes

Polymerase chain reaction (PCR) reaction (Primestar DNA polymerase, Takara) had a total volume of 50 μl, consisting of 10 μl 5× buffer, 4 μl dNTP, 1.5 μl forward primer, 1.5 μl reverse primer, 0.5 μl Primestar enzyme, 1 μl template, and 31.5 μl H$_2$O. Primer sequences are shown in Table 1 below. The amplification conditions were: 1) 94° C. 2 min, 2) 98° C. 15 s, 3) 55° C. 15 s, 4) 72° C. 3 min, 5) 72° C. 10 min, 6) 16° C. 10 min, where steps 2-4 cycled 30 times. Then the PCR products were separated on 1% agarose (Biowest, Spain) gel electrophoresis; the purification was performed completely in accordance with the instruction of purification kit (Omega), and finally the DNA fragments were eluted with de-ionized water.

TABLE 1

Forward and reverse primer sequences for amplification of the cassettes by PCR

| Cassettes | Primer sequences |
| --- | --- |
| | F: caaagaatggatgggaggagttcaggaagccgggga gagggcccgcggcgacattgattattgactagttattaa tag (SEQ ID NO 37) R: ccgcaccaaccgccagaagagccaaagtcaacaca acaacgccttaaatgaggcggccgcactagtgatagatc t (SEQ ID NO 38) |
| | F: cgaccgtggtgtatgtctggtgtgtggcgtccgatc ccgttactatcaccacattgattattgactagttattaa tag (SEQ ID NO 39) R: cgtgtcgtttttaaaaaacccacaatcgccggggtt gagggggggggacgttcaggtggcacttttcggggaaa tg (SEQ ID NO 40) |

(3.4) Construction of H129-G2 by Electroporation of Cassette pRK-CMV-GFP-Zeo and Homologous Recombination 300 ng cassette DNA (about 5-15 μl) was added into and with H129-G1 containing Escherichia coli competent cells prepared in step (2); electroporation conditions were 1.6/1.8 kv, 25 uF and 200Ω, 1 mm; after electroporation, quickly added media and uniformly mixed, transferred to 1.5 ml EP tubes and cultured at 32° C. for 1-2 hours. The bacteria were evenly coated on LB plate containing the corresponding screening resistance, cultured at 32° C. for 36-48 h; colonies were selected and verified by PCR.

(3.5) Preparation of E. coli Competent Cells Containing H129-G2

E. coli competent cells containing H129-G2 were prepared using the same method as described in step (3.2).

(3.6) Construction of H129-G3 by Electroporation of Cassette pRK-CMV-mGFP-Kan and Homologous Recombination Construction of H129-G3 by electroporation of cassette pRK-CMV-mGFP-kan and homologous recombination was performed using the similar procedures as described in step (3.4) except for use of H129-G2 E. coli competent cells prepared in step (3.5).

(3.7) Rescue H129-G3 Virus

The monoclone bacteria cells verified for containing H129-G3 were inoculated into 200 ml LB media, and cultured at 32° C. overnight; then extracted DNA using kit (MN Company) according to its instructions; and finally the extracted DNA was dissolved in de-ionized water. The day before transfection, VERO cells were seeded onto 6-well plates until about 80% confluence. VERO cells were transfected with the above extracted H129-G3 DNA. Transfection mixtures were prepared as follows: 2 µg cyclic H129-G3 DNA, 10 µl SuperFect Transfection Reagent, and serum- and antibiotic-free DMEM culture media were mixed into 100 µl mixture, placed at room temperature for 5-10 minutes, then diluted with 600 µl serum- and antibiotics-free DMEM diluted to form the transfection mixture. The medium was removed, cells were washed with pre-warmed PBS, the transfection mixture was added, and cultured in incubator. After 2-3 hours, the transfection mixture was sucked off; cells were washed once with PBS, and finally added with DMEM medium for culture. Cytopathic effects began about 48 hours after transfection with H129-G3 DNA. When observed under inverted fluorescence microscope, green fluorescence was observed at the pathological lesions, demonstrating that it was a success for rescuing infectious virus clone. And then continuing the culture until all cells were cytopathic, supernatant was collected, that contains H129-G3 recombinant virus, adding 1% of the DMSO for storage at −80° C.

(4) Construction of H129-G4

H129-G4 was constructed based on H129-G1.

(4.1) Knock-Out Loxp Sequence from the Left End of the BAC Sequence (4.1.1) Cassette Kan (i.e. kan$^R$ gene) was amplified by PCR, where the template was derived from plasmid pGBK-T7 (Clonetech, K1612-1). The amplified cassette Kan was used for replacing the loxP and cam$^R$ gene located at the left end of BAC sequence; forward primer (F): tttattgccgt-catagcgcgggttccttccggtattgtctccttccgtgttcgctcagaagaactgt-caagaaggc (SEQ ID NO 41); reverse primer (R): cgggcgt-attttttgagttatcgagattttcaggagctaaggaagctaaaatgattgaacaaga-tggattgcacgc (SEQ ID NO 42). PCR reaction (Primestar DNA polymerase, Takara) had a total volume of 50 µl, consisting of 10 µl 5× buffer, 4 µl dNTP, 1.5 µl forward primer, 1.5 µl reverse primer, 0.5 µl Primestar enzyme, 1 µl template, and 31.5 µl H$_2$O. The amplification conditions were: 1) 94° C. 2 min, 2) 98° C. 15 s, 3) 55° C. 15 s, 4) 72° C. 1 min, 5) 72° C. 10 min, 6) 16° C. 10 min, where steps 2-4 cycled 30 times. Then the PCR products were separated on 1% agarose (Biowest, Spain) gel electrophoresis; the purification was performed completely in accordance with the instruction of purification kit (Omega), and finally the DNA fragments were eluted with 30 µl de-ionized water.

(4.1.2) Preparation of E. coli Competent Cells Containing H129-G1

E. coli competent cells containing H129-G1 were prepared using the same method as described in step (3.2).

(4.1.3) Construction of H129-BAC-DLloxp by Electroporation of Cassette Kan and Homologous Recombination Construction of H129-BAC-DLloxp by electroporation of cassette kan and homologous recombination was performed using the similar procedures as described in step (3.4) except for use H129-BAC E. coli competent cells prepared in step (4.1.2). For PCR verification, forward primer (F): caacac-ccgtgcgttttattc (SEQ ID NO 43), and reverse primer (R): gtaagaggttccaactttcacc (SEQ ID NO 44) were used.

(4.2) Construction of H129-BAC-mGFP-2A-GFP, and Knock-Out Loxp Sequence from the Right End of BAC Sequence (4.2.1) Construction of Cassette CMV-Promoter-mGFP-2A-GFP-Zeo$^R$ for Replacing the Loxp Sequence and SV40-Promoter-GFP at the Right End of BAC Construction of vector pRK-OFP-zeo: inserted resistance gene zeocin into vector pRK-GFP between BamH I and EcoR I; zeocin has an independent EM7 promoter; forward primer (F): cgggatcccaagtttcgaggtcgagtgtc (SEQ ID NO 45); reverse primer (R): gcgaattcggaacggaccgtgttgacaa (SEQ ID NO 46). Construction of vector pRK-mGFP-2A-GFP-zeo: inserted mGFP-2A sequence into vector pRK-GFP-zeo between Hind III and Sal I (removed the mGFP termination codon); forward primer (F): cccaagcttatgctgtgctgtatgagaag (SEQ ID NO 47); reverse primer (R): cggtcgactgggccaggat-tctcctcgacgtcaccgatgagcagatcctctgccctccttgtacagctcgtcc (SEQ ID NO 48).

(4.2.2) PCR Amplification of Cassette CMV-Promoter-mGFP-2A-GFP-Zeo$^R$

The template was vector pRK-mGFP-2A-GFP-zeo, where forward primer (F): aggtaccttctgaggcggaaagaaccagtg-gaatgtgtgtcagttagacattgattattgactagttattaatag (SEQ ID NO 49); reverse primer (R): tctgcgacctggcgcgcacgtttgcccggga-gatggggaggctaactgaggaacggaccgtgttgacaattaatc (SEQ ID NO 50); and the steps of PCR reaction and purification of DNA product were similar to the step (4.1.1).

(4.2.3) Preparation of E. coli Competent Cells Containing H129-BAC-DLloxp

E. coli competent cells containing H129-BAC-DLloxp were prepared using the same method as described in step (3.2).

(4.2.4) Construction of H129-BAC-mGFP-2A-GFP by Electroporation and Homologous Recombination Construction of H129-BAC-mGFP-2A-GFP by electroporation of cassette CMV-promoter-mGFP-2A-GFP-Zeo$^R$ and homologous recombination was performed using the similar procedures as described in step (3.4). For PCR verification, forward primer (F): acctctgaaagaggaacttgg (SEQ ID NO 51), and reverse primer (R): gatggtccagac-ccacgtcac (SEQ ID NO 52).

(4.3) Construction of H129-mGFP-2A-GFP-BAC-mGFP-2A-GFP (i.e. H129-G4)

(4.3.1) Construction of Cassette CMV-Promoter-mGFP-2A-GFP-Cam

Inserted into vector pRK-mGFP-2A-GFP-Zeo resistance gene cam downstream of BamH I, cam has an independent cat promoter; forward primer (F): cgggatcctgatcggcacg-taagaggttc (SEQ ID NO 53), reverse primer (R): cgggatc-cttacgccccgccctgccactcat (SEQ ID NO 54).

(4.3.2) PCR Amplification of Cassette CMV Promoter-mGFP-2A-GFP-Cam$^R$

The template was plasmid pRK-mGFP-2A-GFP-cam, where forward primer (F): caagaatggatggagattcaggaagc-cgggagagggcccgggacattgattattgactagttataatag (SEQ ID NO 55); reverse primer (R): ccgcaaacccgccagaagagccaaagt-caacacaacaacgccttaaatgtgatggcacgtaagaggttcaac (SEQ ID NO 56); and the steps of PCR reaction and purification of DNA product were similar to the step (4.1.1).

(4.3.3) Preparation of *E. coli* Competent Cells Containing H129-BAC-mGFP-2A-GFP

*E. coli* competent cells containing H129-BAC-mGFP-2A-GFP were prepared using the same method as described in step (3.2).

(4.3.4) Construction of H129-G4 by Electroporation and Homologous Recombination

Construction of H129-G4 by electroporation of cassette CMV promoter-mGFP-2A-GFP-cam$^R$ and homologous recombination was performed using the similar procedures as described in step (3.4). For PCR verification, forward primer (F): cggaaaccaaagaaggaagc (SEQ ID NO 57), and reverse primer (R): gggagcccaacaaacagcac (SEQ ID NO 58).

(4.3.5) Rescue H129-G4 Virus

H129-G4 virus was rescued following the similar protocol of step (3.7).

(4.3.6) Growth Comparison Between H129-wt Virus and Recombinant Viruses

Growth curve comparison was performed following the step (2.13). Referring now to FIG. 2(e), there is provided a graph showing the growth curves of H129-wt, H129-G1, H129-G3 and H129-G4 in VERO cells. VERO cells were infected with H129-wt, -G1, -G3 or -G4 at an MOI of 3, and the progeny virus in the supernatant at the indicated times were determined by standard plaque forming assay. Shown is the mean±SD (standard deviation) from 3 independent experiments. As shown in FIG. 2(e), the replication kinetics of H129-wt, -G1, -G3 and -G4 were similar, demonstrating that the insertion location within H129 genome is flexible.

(5). Fluorescence Intensity of H129-G1, H129-G3 and H129-G4 in VERO Cells

Figure 3:
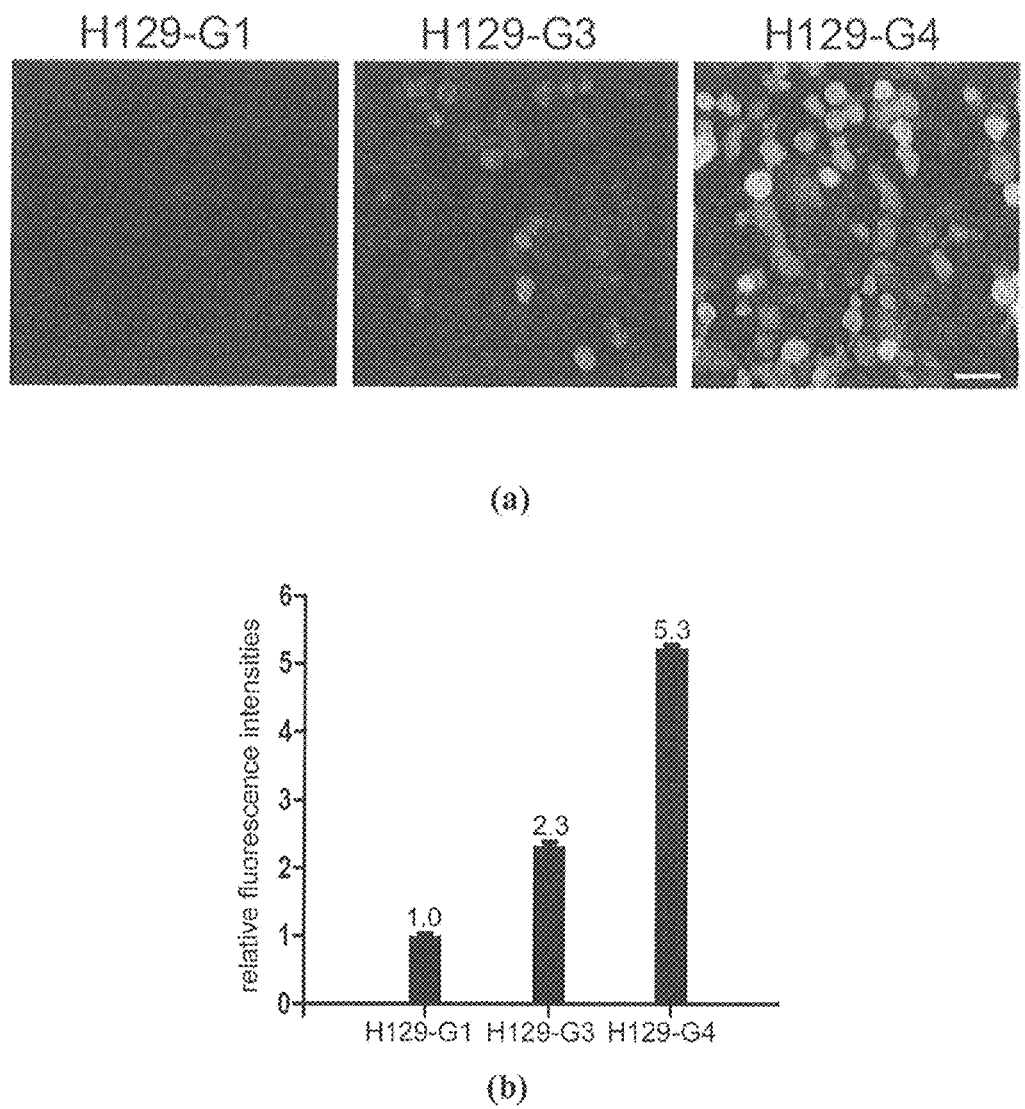
FIG. 3 presents (a) images and (b) a graph showing the fluorescence intensities of H129-G1, H129-G3 and H129-G4 in vitro.

Referring now to FIG. 3, there are provided with (a) images and (b) a graph showing the fluorescence intensities of H129-G1, H129-G3 and H129-G4 In vitro. VERO cells were infected with H129-G1, H129-G3 and H129-G4 at an MOI of 1, respectively, and the GFP signal was observed at 24 hpi. Images were taken under the same condition. Scale bar=50 μm. As shown in FIG. 3(b), H129-G4 is about 5.3 times higher than H129-G1 while H129-G3 is about 2.3 times higher than H129-G1; it implies that the fluorescence intensity is not a simple addition of the fluorescence genes.

(6). Microfluidic Device

Figure 4:
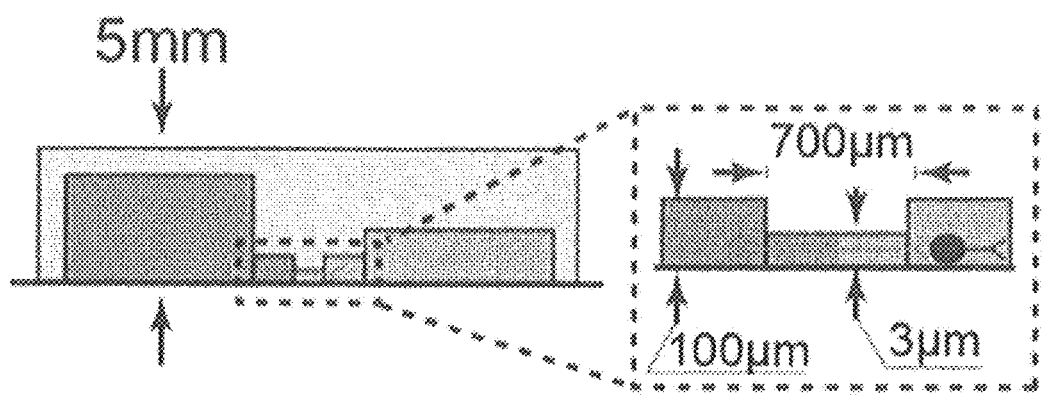
FIG. 4 shows a schematic structure diagram of the microfluidic system.

Referring now to FIG. 4, there is provided a schematic structure diagram of the microfluidic device. As shown in FIG. 4, the microfluidic device comprises two isolated culture chambers that are connected by multiple microchannels, where the multiple microchannels only allow the axons grow-through but completely impede the dendrites. Microfluidic device was fabricated following the protocol described previously [21, 23, 24].

(7). Culture of Neurons in Microfluidic Device

To culture neurons in the microfluidic device, freshly isolated fetal mouse hippocampal neurons ($2.5 \times 10^6$, in 500 μl media) were plated into one chamber (blue chamber in FIGS. 5(a) and (b)) (Day 1). For bi-chamber culture, a new batch of neurons ($6.25 \times 10^5$ neurons in 250 μl) was added into the opposite chamber (red chamber in FIGS. 5(c) and (d)) at Day 5 when the axons of first plated neurons grew into the microchannels. Medium was refreshed every day, and the volume in the efferent and afferent end chamber was always maintained at 500 μl and 250 μl, respectively. To guide the directional growth of axons in the microchannels, the higher hydrostatic pressure is generated by the larger medium volume in the efferent chamber; to prevent the reversed axonal growth, less number of neurons are plated at 4 days later (Day 5). For infection, H129-G4 was added into either chamber as in FIGS. 5(a) and (c) to reach a final concentration of $1 \times 10^7$ pfu/ml at the indicated time point. To avoid virus diffusion to the opposite chamber, the medium volume in the infection chamber was maintained half less than the opposite one. Images were taken at 24 hours post infection (hpi).

(8). Intracerebral Virus Injection

Intracerebral virus injection was performed using a stereotaxic system in a BSL-2 animal facility following the approved SOP on adult wild-type C57BL/6, DAT-Cre mice, PV-Cre mice, and tree shrews. DAT-Cre transgenic mice specifically express Cre recombinase in dopaminergic (DA) neurons under the control of the dopamine transporter (DAT) promoter; PV-Cre transgenic mice express Cre recombinase in parvalbumin (PV) interneurons. Both are of C57BL/6 background. The anesthetized animals received intracerebral virus injection with a motorized stereotaxic injector (Stoelting Co.). The exact location of the mouse nuclei was determined according to the Mouse Brain Atlas by the mediolateral (ML), anteroposterior (AP) and dorsoventral (DV) distances to Bregma [25], and the coordinates for tree shrew nuclei were determined according to the Tree Shrew Brain Atlas [26]. When indicated, Alexa Fluor 594 conjugated-cholera toxin B subunit (CTB) (Invitrogen) was injected along with the virus. The injection details are listed in Table 1.

TABLE 1

Injection sites and H129-derived tracers

| Animal | Virus | Nucleus | Coordinates (mm) ML | AP | DV | Dose (pfu) | Volume (μl) | Animal number |
|---|---|---|---|---|---|---|---|---|
| Tree shrew | H129-G3 | VPM | +1.40 | −1.82 | −3.62 | $1 \times 10^6$ | 0.3 | 8 |
|  | H129-G4 | M1 | +2.00 | +2.10 | −1.88 | $1 \times 10^6$ | 0.2 | 8 |
|  | H129-G4 | GCL | +1.15 | +3.92 | −2.00 | $1 \times 10^6$ | 0.2 | 3 |
|  | H129-G4 | subretina | NA | NA | NA | $1 \times 10^6$ | 1.0 | 3 |
|  | H129-G4 | M1 | −2.60 | +1.85 * | +2.10 | $2 \times 10^6$ | 0.3 | 5 |

* interaural instead of AP

For intracerebral virus injection, 8-10 week-old male mice or adult male tree shrew were applied without randomization or blinding. Animals were monitored daily after the virus injection, and experiment would be terminated and animal would be excluded if severe sickness was observed.

(9). Two-Photon Fluorescence Micro-Optical Sectioning Tomography (fMOST)

Specimen for fMOST imaging was embedded with Technovit® 9100 Methyl Methacrylate (MMA, Electron Microscopy Sciences) as described previously[27]. Briefly, PFA fixed animal brain was rinsed in 0.01M PBS for 12 h, and completely dehydrated in a series of alcohol (50%, 75%, 95%, 100% and 100% ethanol, 2 h for each) followed by immersion in xylene twice (2 h for each) for transparentization. Then the specimen was infiltrated, transferred into gelatin capsule and immersed in polymerization solution. Finally, the capsule with the specimen was closed and kept in a dry chamber at 4° C. in dark for 72 h. After complete polymerization, the whole brain was imaged using fMOST system with a data acquisition rate at 0.5 μm×0.5 μm×1 μm pixel size[28]. Lastly, the image stack of the acquired data set was transformed into Large Data Access using the Amira software (Visage Software, USA) for 3D image reconstruction [29].

(10). Anterograde Transmissions of H129-G4 in Cultured Neurons

Figure 5:
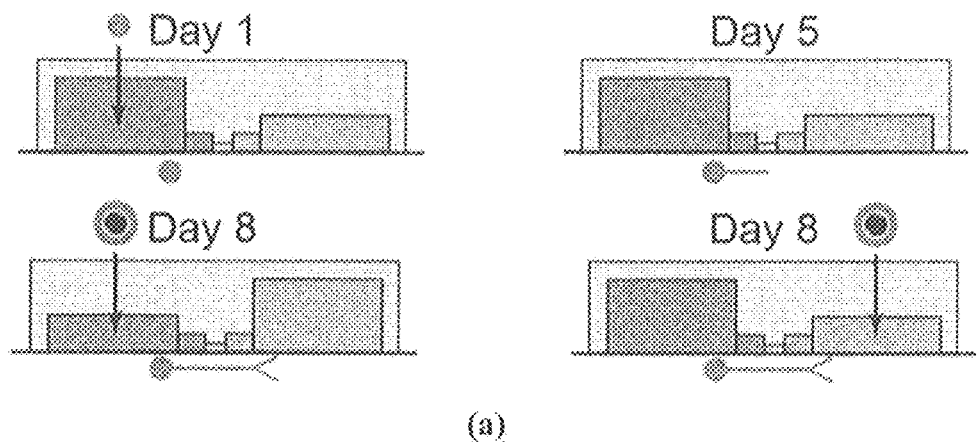
FIG. 5 shows the anterograde transmissions of H129-G4 in cultured neurons. (a-b) Soma entry and anterograde labeling of H129-G4; (c-d) Anterograde transneuronal labeling of H129-G4.
Figure 5:
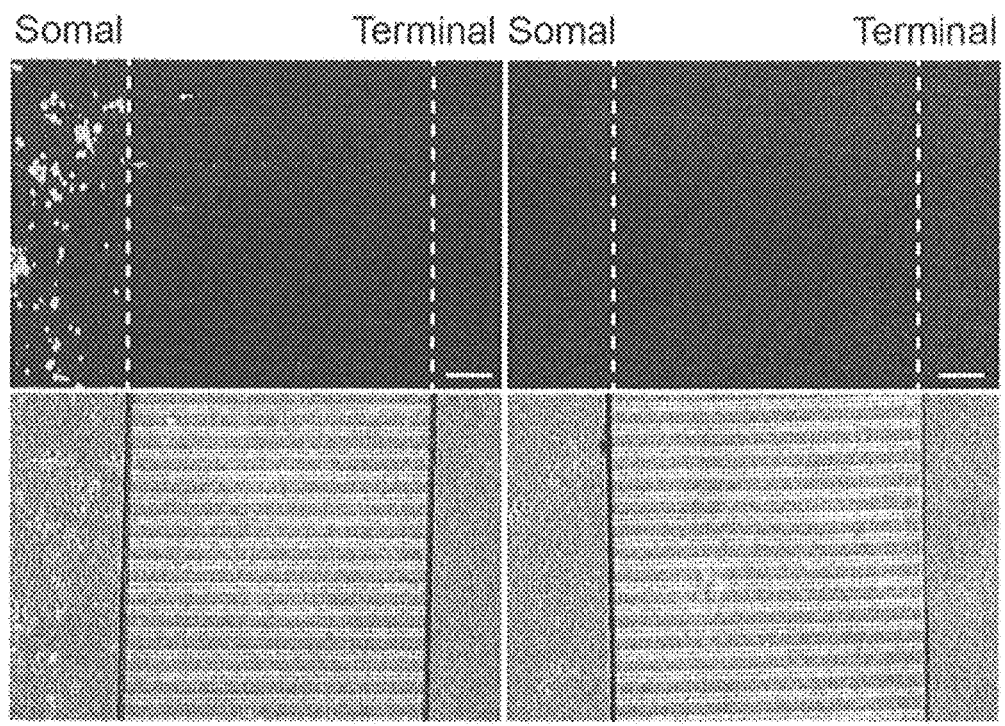
Figure 5:
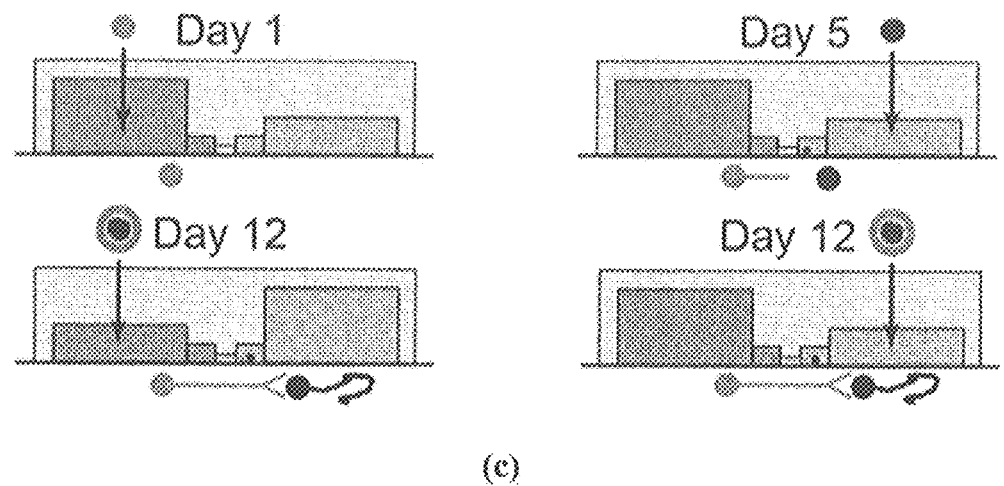
Figure 5:
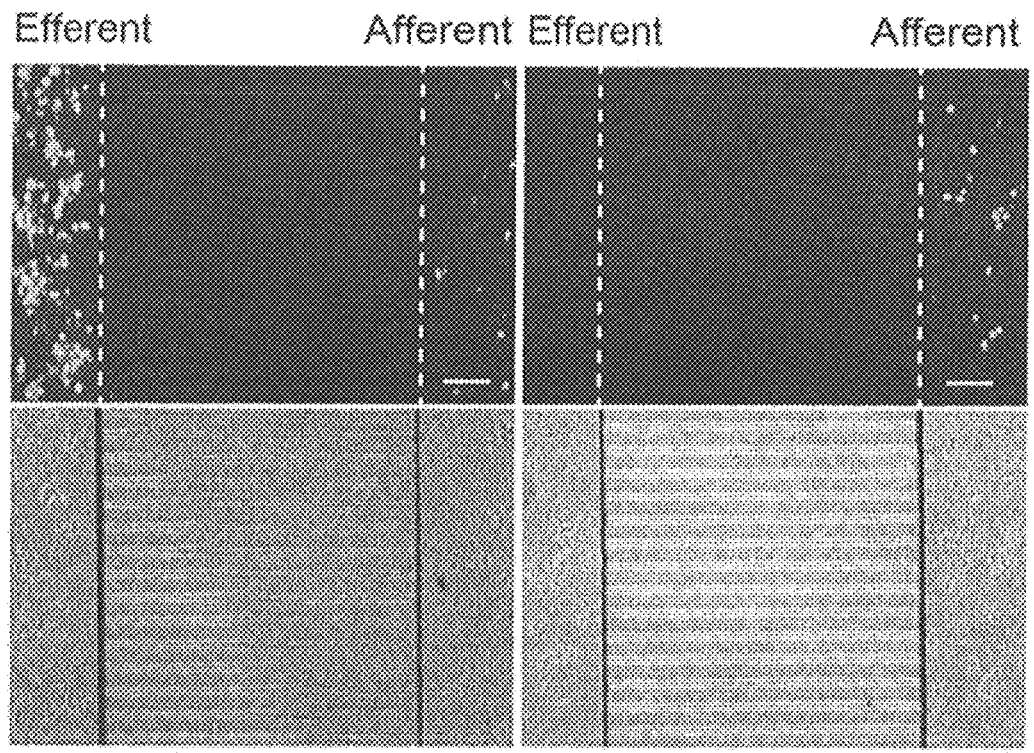

Referring now to FIG. 5, there are shown the anterograde transmissions of H129-G4 in cultured neurons. (a-b) Soma entry and anterograde labeling of H129-G4. Freshly isolated fetal mouse hippocampal neurons were seeded into one chamber of the microfluidic device, and termed the first 24 h as Day 1, and H129-G4 was added at Day 8 into the chamber of either somal (blue) or axonal terminal chamber (red) to a final concentration of $10^7$ pfu/ml (a). The representative results of somal- and axonal terminal-side infection are presented in the left and right panel, respectively. Images of GFP signal (upper panel) and phase contrast (lower panel) were obtained at 24 hour post infection (hpi). The dotted lines indicate the borders between chambers and the microchannels. Scale bar, 100 μm (b). (c-d) Anterograde transneuronal labeling of H129-G4. Neurons were sequentially plated into both chambers at Day 1 and Day 5 respectively, then H129-G4 was added at Day 12 into either the efferent (blue) or afferent chamber (red) to a final concentration of $10^7$ pfu/ml (c). The representative results of efferent- and afferent-side infection are presented in the left and right panel, respectively. Images of GFP signal (upper panel) and phase contrast (lower panel) were obtained at 24 hpi. The dotted lines indicate the borders between chambers and the microchannel. Scale bar, 100 μm (d).

When H129-G4 was added to the soma side (FIG. 5(a)), neurons and their axons were labeled with GFP by 24 hours post infection (hpi) (FIG. 5(b)). However, no GFP labeled neuron was observed when the virus was added into the axonal terminal side (FIG. 5(b), right panels). These data indicate that H129-G4 barely infects neuron through their terminals at the indicated virus dose and at the indicated observation time post infection.

When H129-G4 was added to the efferent neurons, H129-G4 was capable of spreading through the axons in the microchannels and labeling the afferent neurons in the opposite chamber with GFP (FIG. 5(d), left panel). However, when H129-G4 was added to the afferent chamber, GFP positive neurons were only observed in the same chamber, and no neuron was labeled in the efferent chamber (FIG. 5(d), right panels). These data indicate that H129-G4 transmits between the cultured neurons in the microfluidic device in a strict anterograde transsynaptic manner at the indicated virus dose and at the indicated observation time.

(11). Tracing Time Course of VPM-S1 Circuit Using H129-G3

Figure 6:
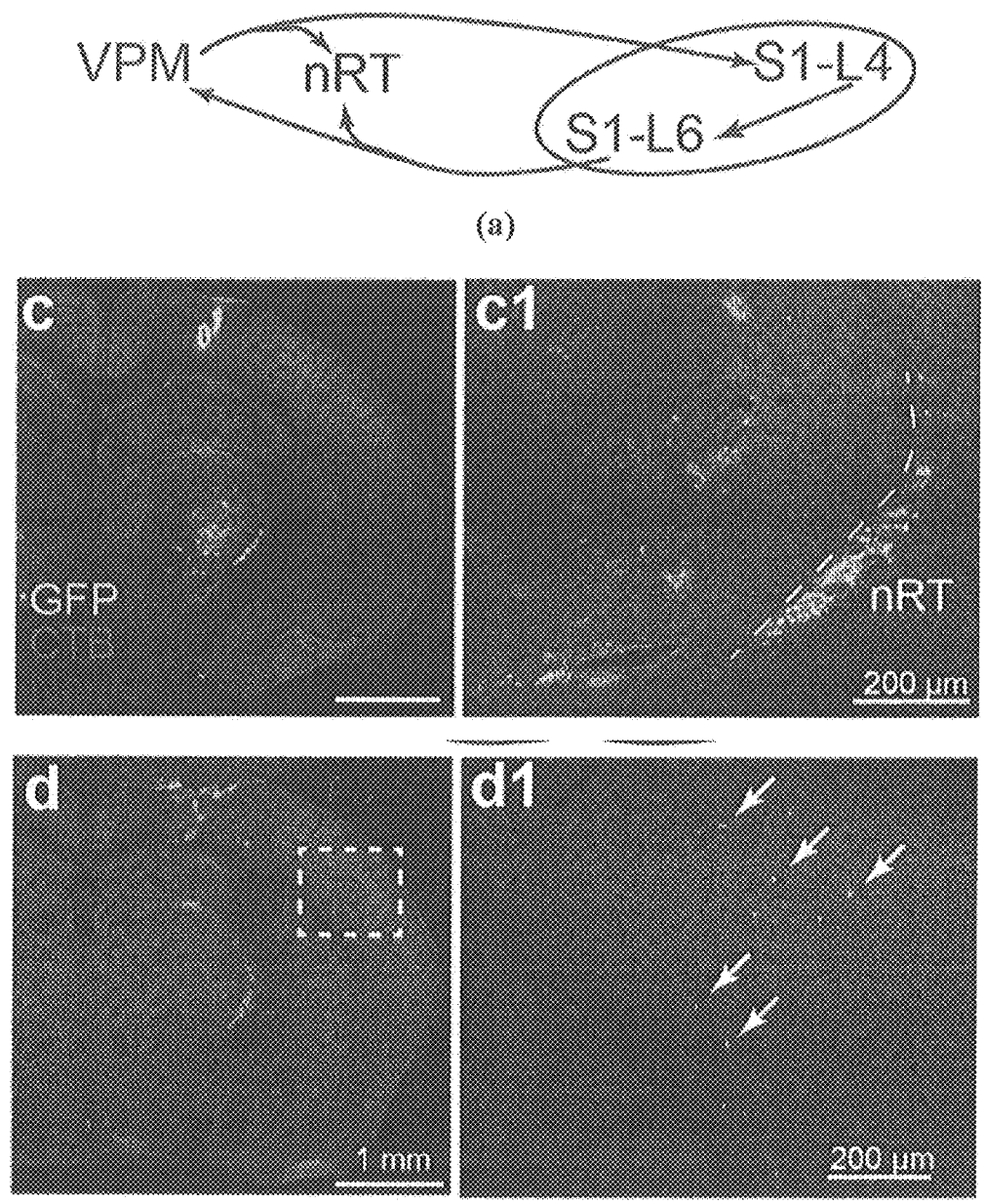
FIG. 6 shows the tracing time course of VPM-S1 circuit using H129-G3.
Figure 6:
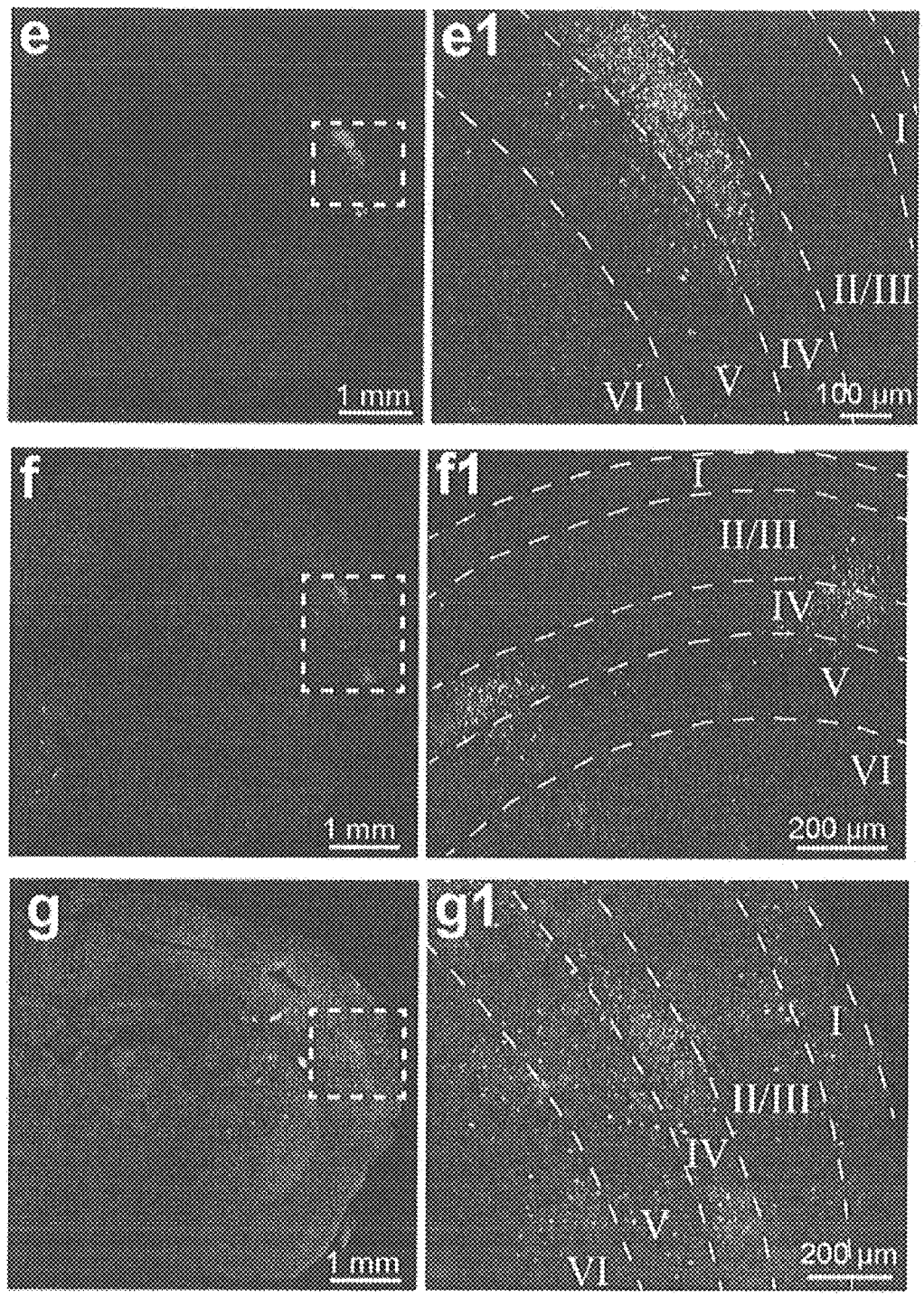
Figure 6:
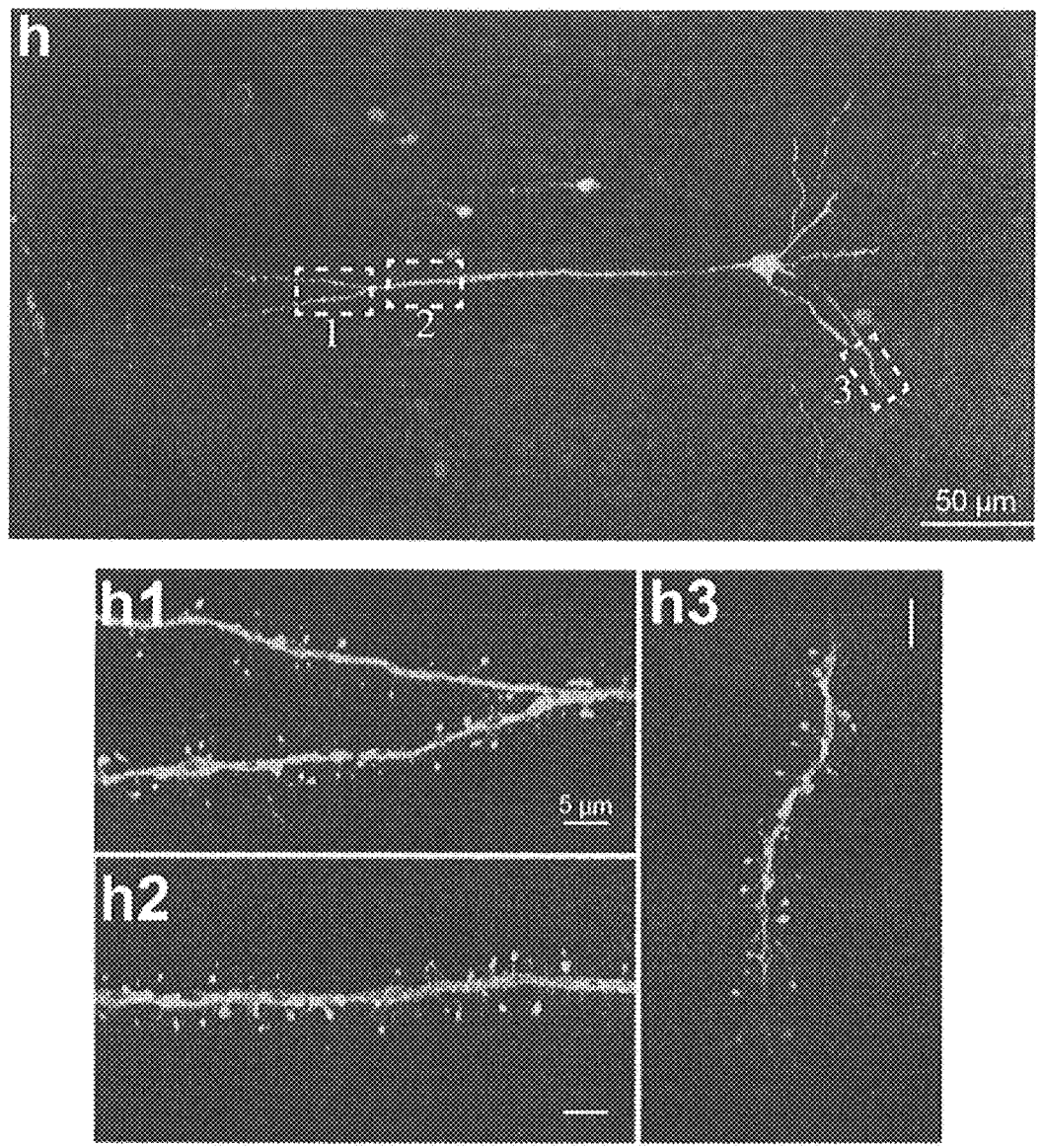

Referring now to FIG. 6, there is provided the tracing time course of VPM-S1 circuit using H129-G3. (a) Schema of the VPM-S1 circuit. VPM, ventral posteromedial thalamic nucleus; nRT, nucleus of reticular thalamus; S1, primary somatosensory cortex; L4 and L6, layer IV and VI of the cortex. (c-g) Representative tracing results of H129-G3 in VPM-S1 circuit. H129-G3 ($1\times10^6$ pfu in 300 nl) was injected into the VPM of wild-type C57BL/6 mice together with Alexa Fluor 594-conjugated CTB (CTB, red). The tracing results at 2 (c), 3 (d), 4 (e), and 5 (f) days post injection (dpi) (g) are shown. The boxed areas are magnified and presented in the right panel. The scattered GFP-positive neurons in c1 are indicated with white arrows. (h) A representative GFP-labeled single neuron. A pyramidal neuron was labeled with complete dendritic trees in S1 at 4 dpi. Magnified images of the segments of the apical (h1 and h2) and the basal dendrite (h3) are shown.

H129-G3 ($10^6$ pfu in 300 nl) was injected into the VPM together with Alexa Fluor 594 conjugated-cholera toxin B subunit (CTB), which marks the injection site and retrogradely labels the neuronal soma by axon terminal uptake. We evaluated the labeling direction, efficiency, and transsynaptic transmission of H129-G3 as determined by the infection time course. At 2 day post virus inoculation (2 dpi), both CTB (red) and GFP-positive cells were present at the injection site. GFP-positive neurons were also observed in the nearby nRT (FIG. 6(c)). By 3 dpi, in addition to the GFP signal at nRT (FIG. 6(d)), a few GFP-positive neurons were observed in the cortex (FIG. 6(d1)). By 4 dpi, two segregated cell populations in the ipsilateral S1 were clearly labeled: the GFP-positive cell population in L4, and the CTB-labeled cell population in L6. No overlap was observed between the two populations (FIG. 6(e)). These data indicate that H129-G3 anterogradely and transsynaptically label L4 neurons, but does not retrogradely label L6 neurons via their axon terminals in the VPM. A smaller population of GFP-positive cells was also observed in L4 of the secondary somatosensory cortex (S2) (FIG. 6(f)), suggesting a possible direct VPM-S2 projection. By 5 dpi, H129-G3 spread to other cortical layers including L6 (FIG. 6(g)), while CTB-positive cells remained at L6. These results confirmed that H129-G3 transmits transneuronally, multi-synaptically, and strict anterogradely.

A representative pyramidal neuron with nicely labeled apical and basal dendrites is shown in FIG. 6(h), where individual dendritic spines can be readily detected based on the GFP signal. Notably, while H129-G3 labeling intensity is sufficient for visualizing neuronal structures, it is not enough because the individual axon was not clearly distinguishable.

(12). Mapping of the M1 Projection Output Using H129-G4

Figure 7:
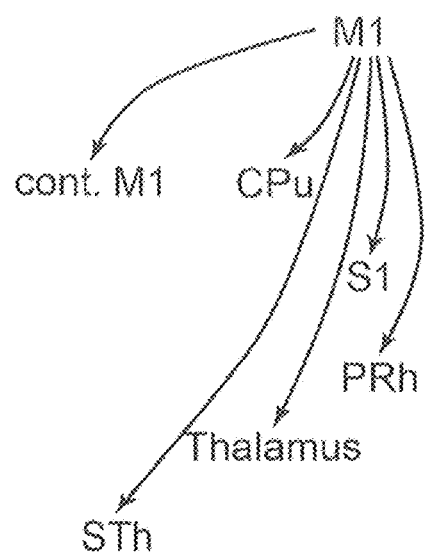
FIG. 7 shows the mapping of the M1 projection output using H129-G4.
Figure 7:
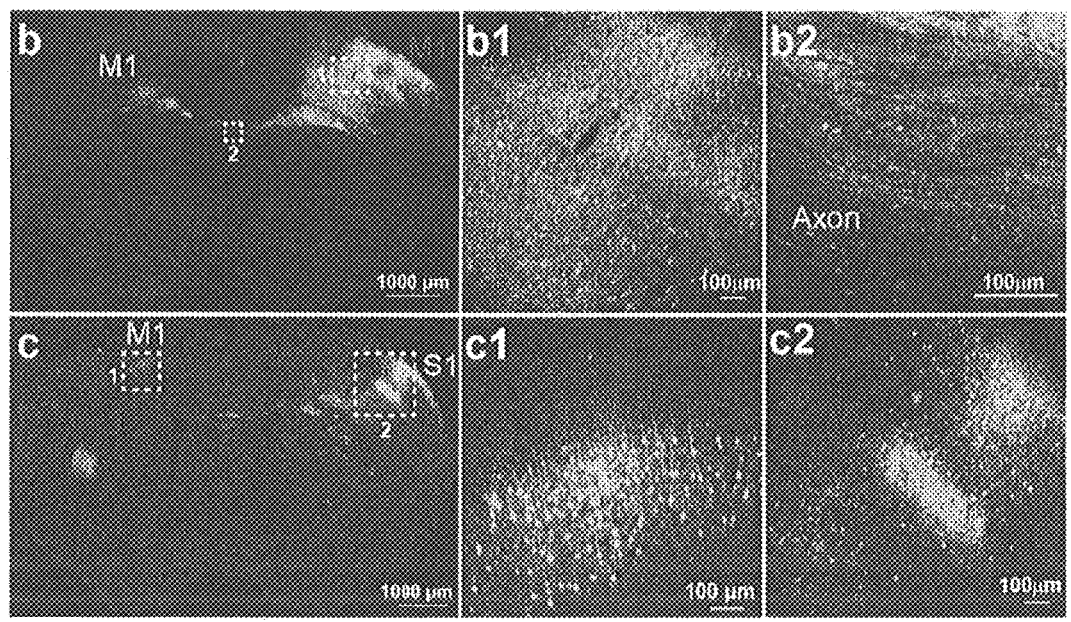
Figure 7:
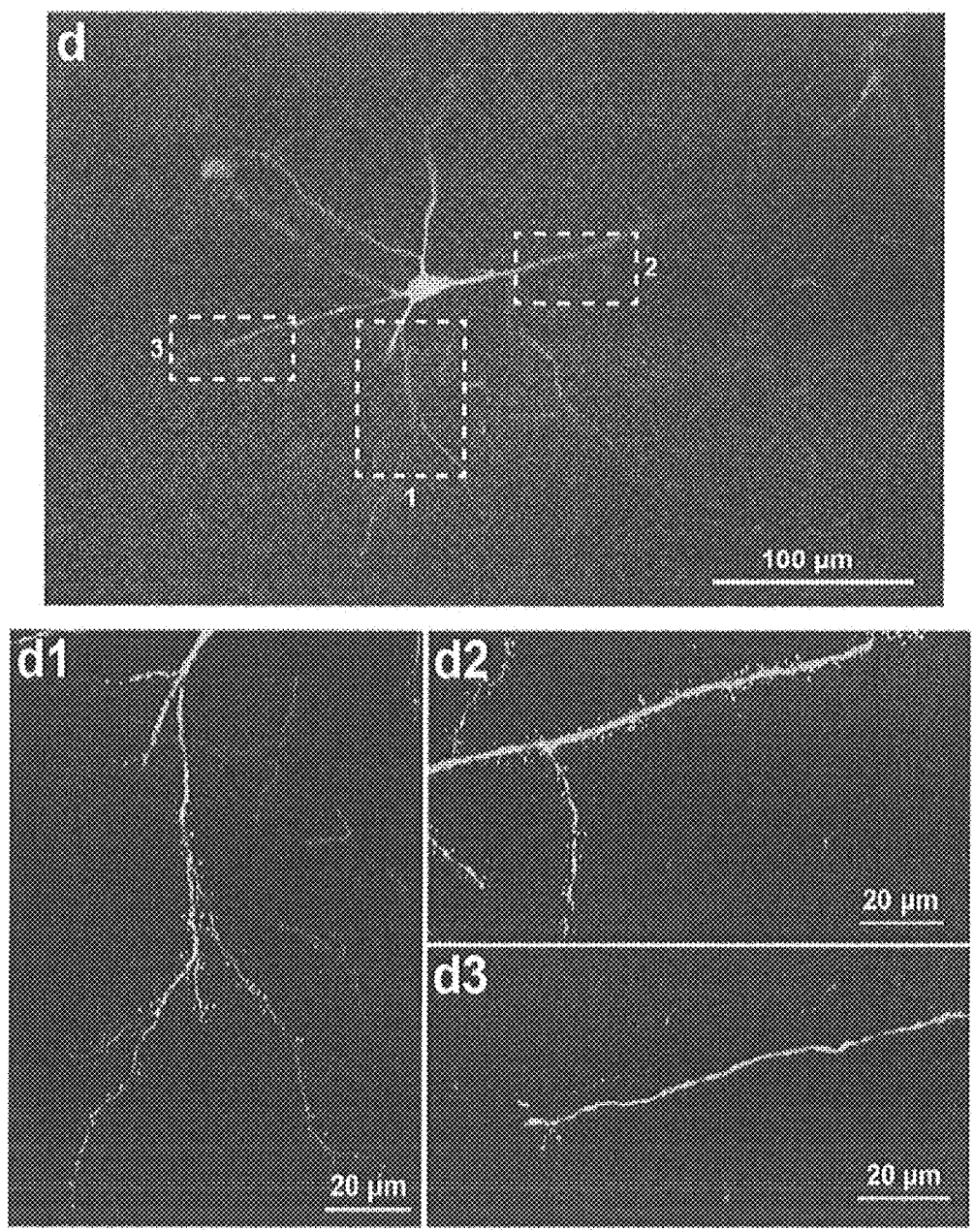
Figure 7:
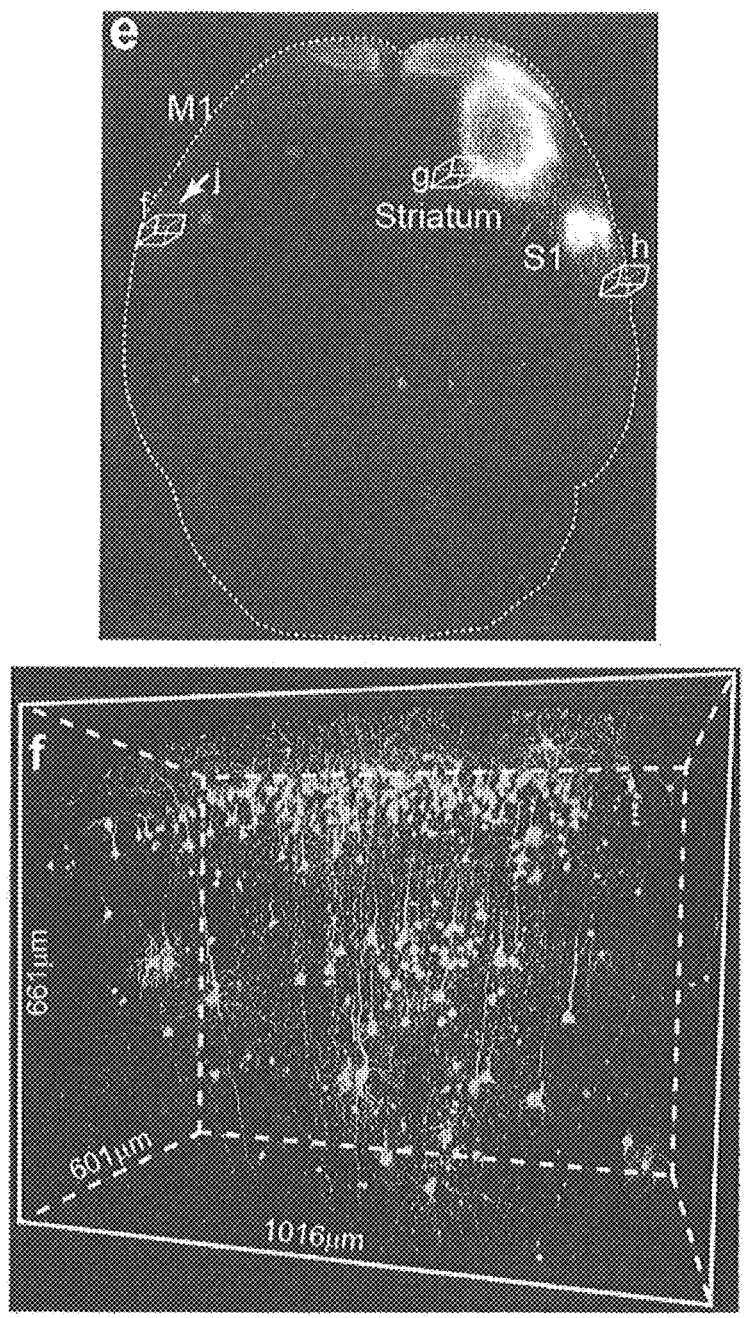
Figure 7:
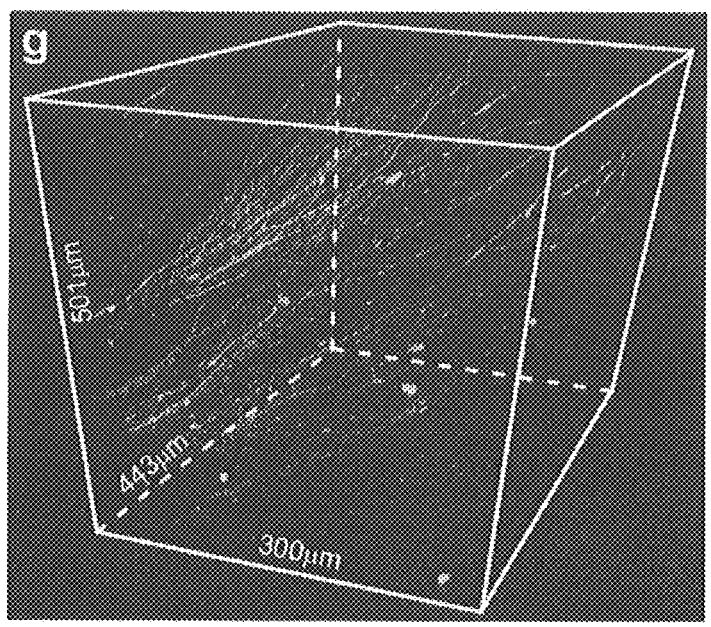
Figure 7:
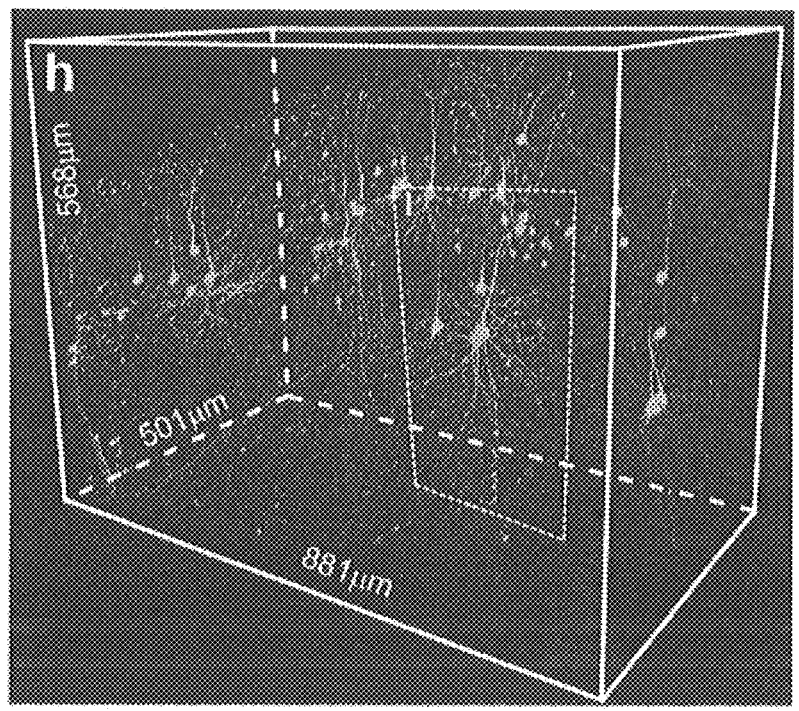
Figure 7:
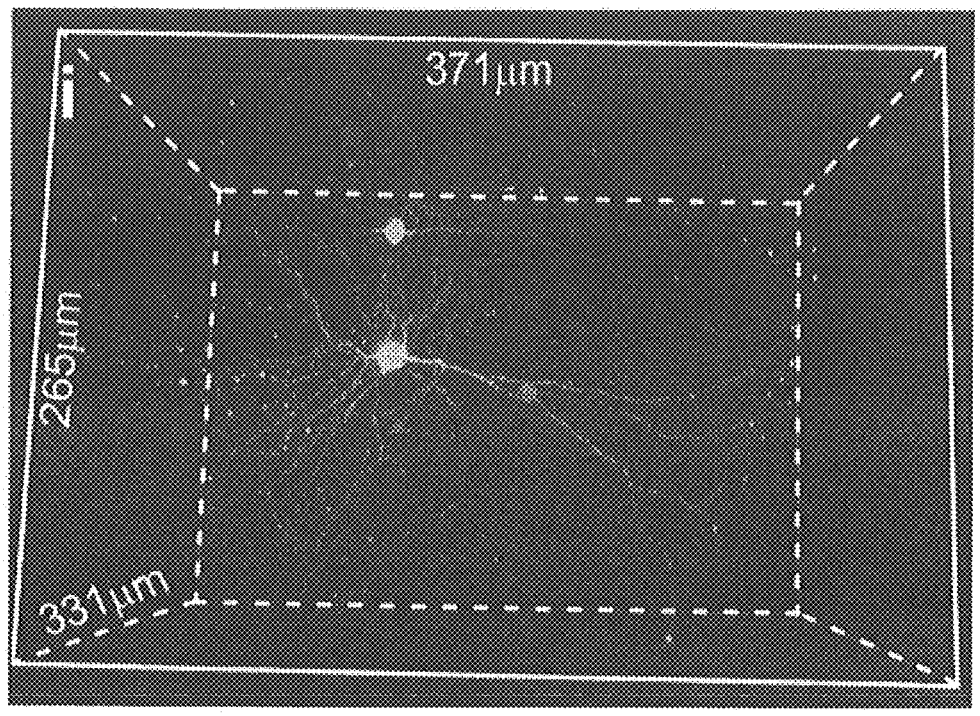
Figure 7:
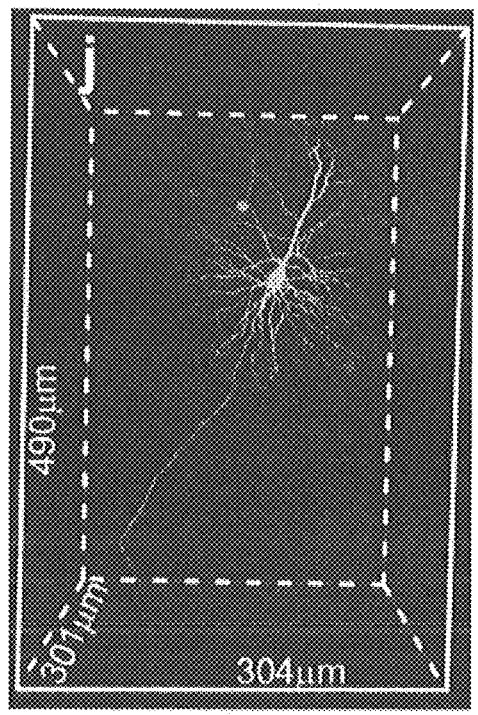

Referring now to FIG. 7, there is shown the mapping of the M1 projection output using H129-G4. (a) Schema of the M1 projection pathways. M1, primary motor cortex; cont. M1, contralateral M1; S1, primary somatosensory cortex; PRh, perirhinal cortex; STh, subthalamic nucleus; CPu, caudate putamen. (b-c) Representative tracing results of M1 projections. H129-G4 ($10^6$ pfu in 200 nl) was injected into the M1 of wild-type C57BL/6 mice, and images of coronal brain sections were obtained at 4 dpi. The boxed regions are shown with a higher magnification. (d) A representative H129-G4 labeled single neuron. A representative GFP-labeled neuron in PRh is shown, and the magnified images of the dendritic segments with individual spines (d1 and d2)

and the axon (d3) are presented in the right. (e-j) Combination of fMOST and H129-G4 tracing. The brain obtained at 4 dpi was further processed to fMOST imaging. The 3D image of the whole brain was reconstructed (e). Representative brain regions innervated by M1, including the cont. M1 (f), striatum (g) and S1 (h), are shown in details. Representative single neurons in the ipsilateral S1 (i) and the cont. M1 (j) are also presented.

Primary motor cortex (M1) is the major cortical region that generates and sends motor control signals to downstream targets. The direct projection from M1 has been well defined (FIG. 7(a)). H129-G4 was applied to this pathway for verification of its anterograde tracing capacity and efficiency. Wild-type C57BL/6 mice were intracerebrally injected with H129-G4 ($10^6$ pfu in 200 nl) at M1, and then examined at 4 dpi. At the injection location in the M1, H129-G4 labeled a massive group of neurons. A substantial group of neurons in the contralateral M1 was also labeled (FIG. 7(b)-(c)). In addition, the fibers connecting the bilateral M1s were clearly visible (FIG. 7(b2)). GFP-labeled neurons were also observed in the ipsilateral S1 (FIG. 7(c2)), reflecting the projection from M1 to S1. Other brain regions innervated by M1 were also labeled, including the thalamus, subthalamic nucleus (STh), perirhinal cortex (PRh), and caudate putamen (CPu) (data not shown). Besides the macroscopic circuit tracing, H129-G4 also revealed the detailed structures of neurons (FIG. 7(d)).

Fluorescence Micro-Optical Sectioning Tomography (fMOST) is a powerful high-throughput imaging system enabling automated reconstruction of neural circuit in the entire brain with high resolution at submicron levels[30]. So far, H129-G4 is the only anterograde transsynaptic viral tracer whose labeling intensity is high enough for fMOST. The general tracing and labeling patterns of H129 revealed by the reconstructed whole brain fMOST image (FIG. 7(e)) were consistent with those detected by confocal microscopy (FIG. 7(b)-(d)). A large population of neurons in the inoculated M1, the contralateral M1 (FIG. 7(f)), and the ipsilateral S1 (FIG. 7(h)) were labeled. The projecting axonal fibers were also clearly visible (FIG. 7(g)). Even in distant regions, the H129-G4 still sparsely labeled neurons with high fluorescence intensity, which made it possible to obtain detailed structure of single neurons and their projections (FIG. 7(i)-(j)). Therefore, H129-G4 is a potent anterograde transsynaptic viral tracer that can be generally used for mapping projection circuits and projection connectome.

(13). Mapping of the M1 Projection Output in Tree Shrew Using H129-G4

Figure 8:
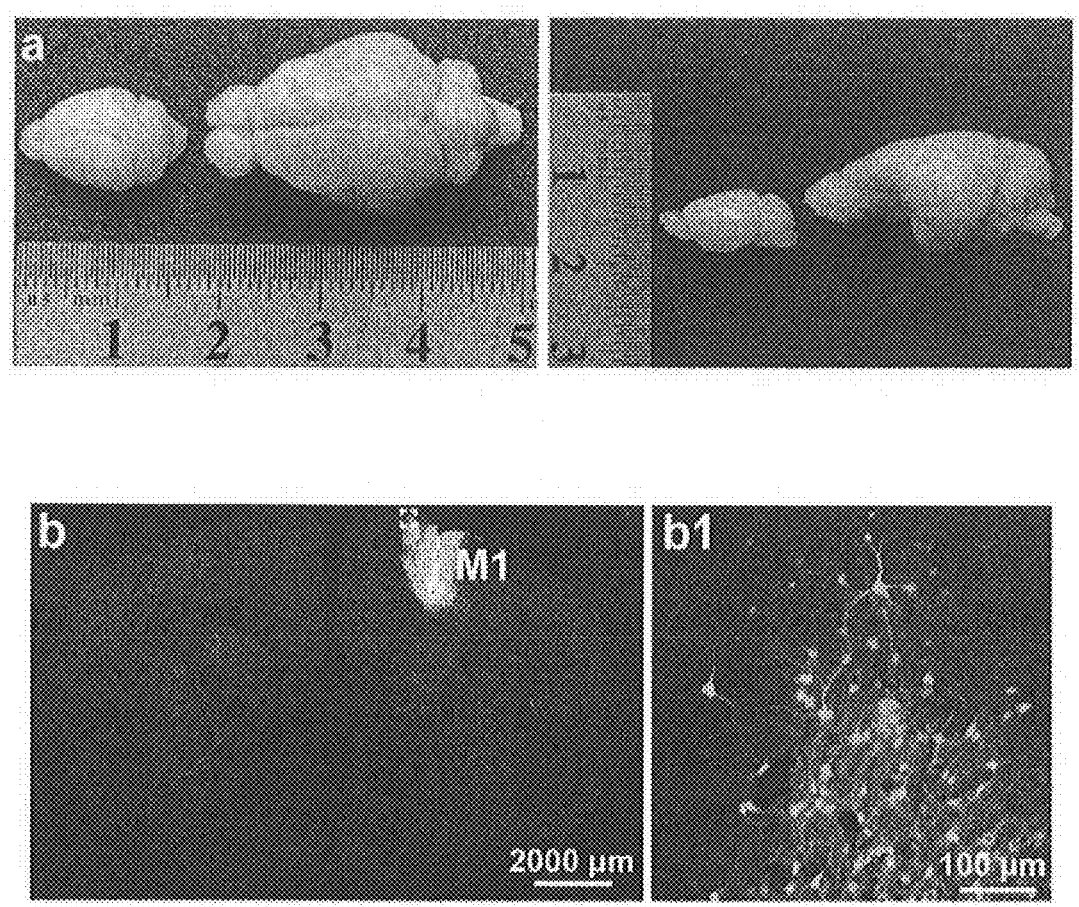
FIG. 8 shows the mapping of the M1 projection output in tree shrew using H129-G4.
Figure 8:
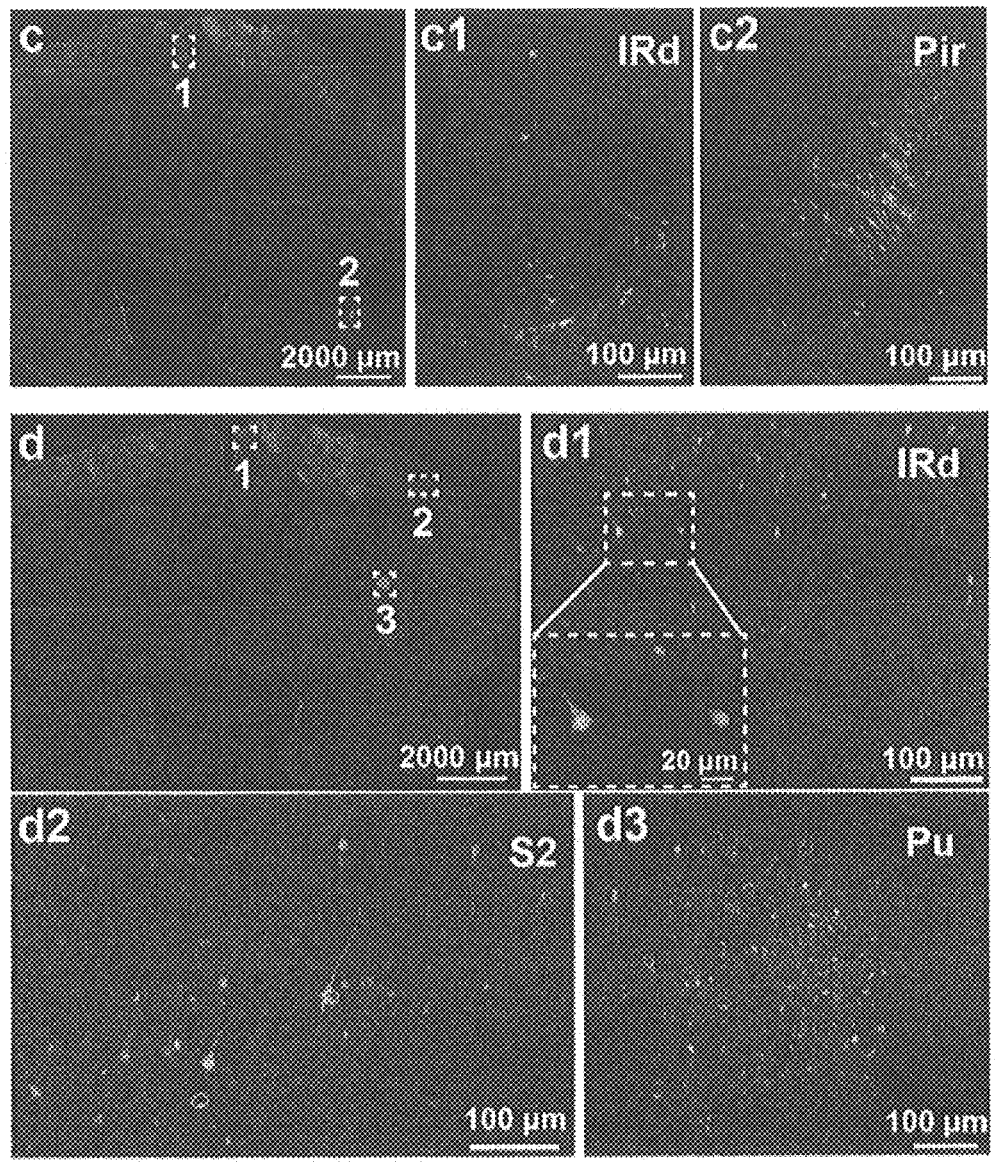
Figure 8:
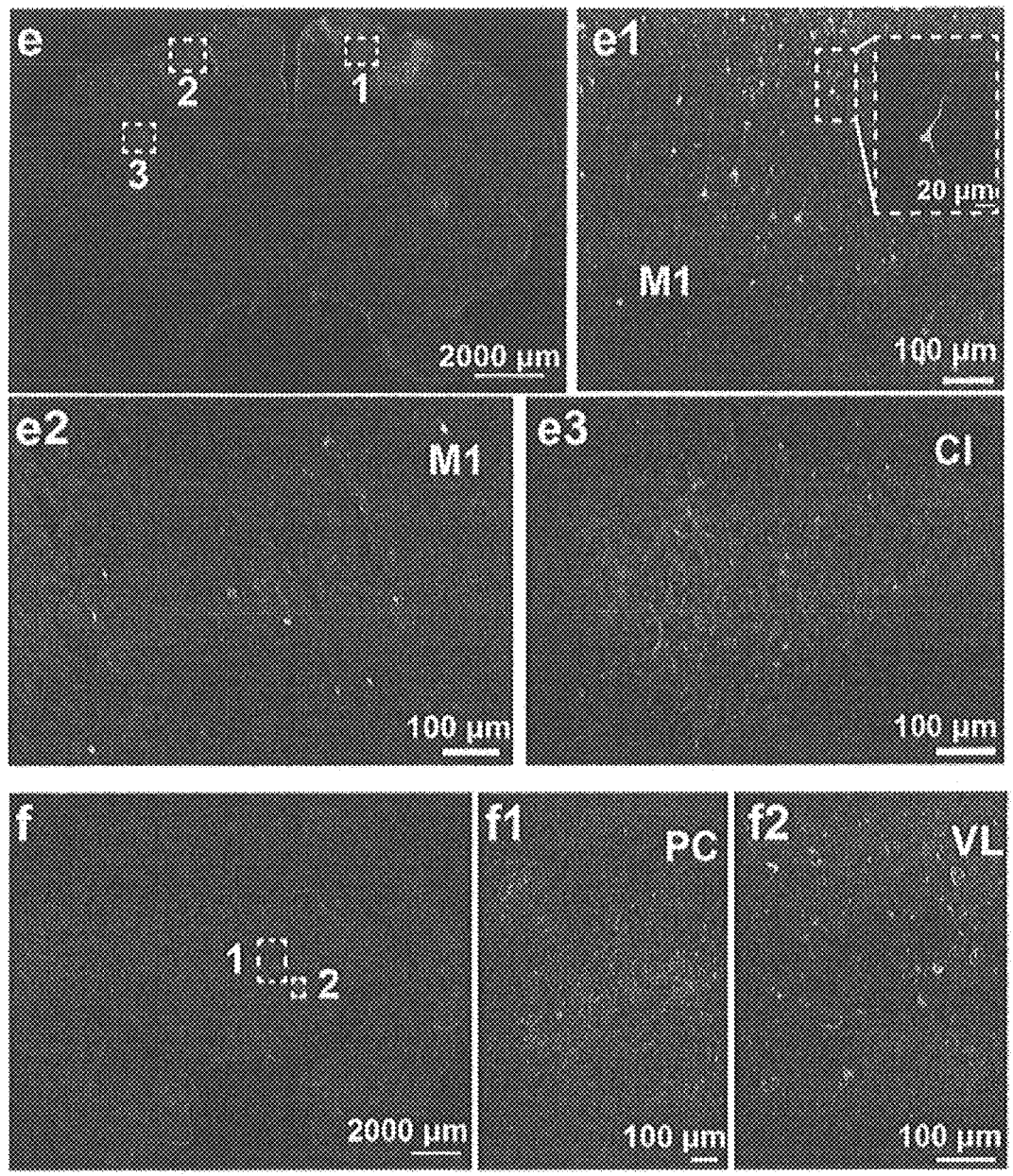
Figure 8:
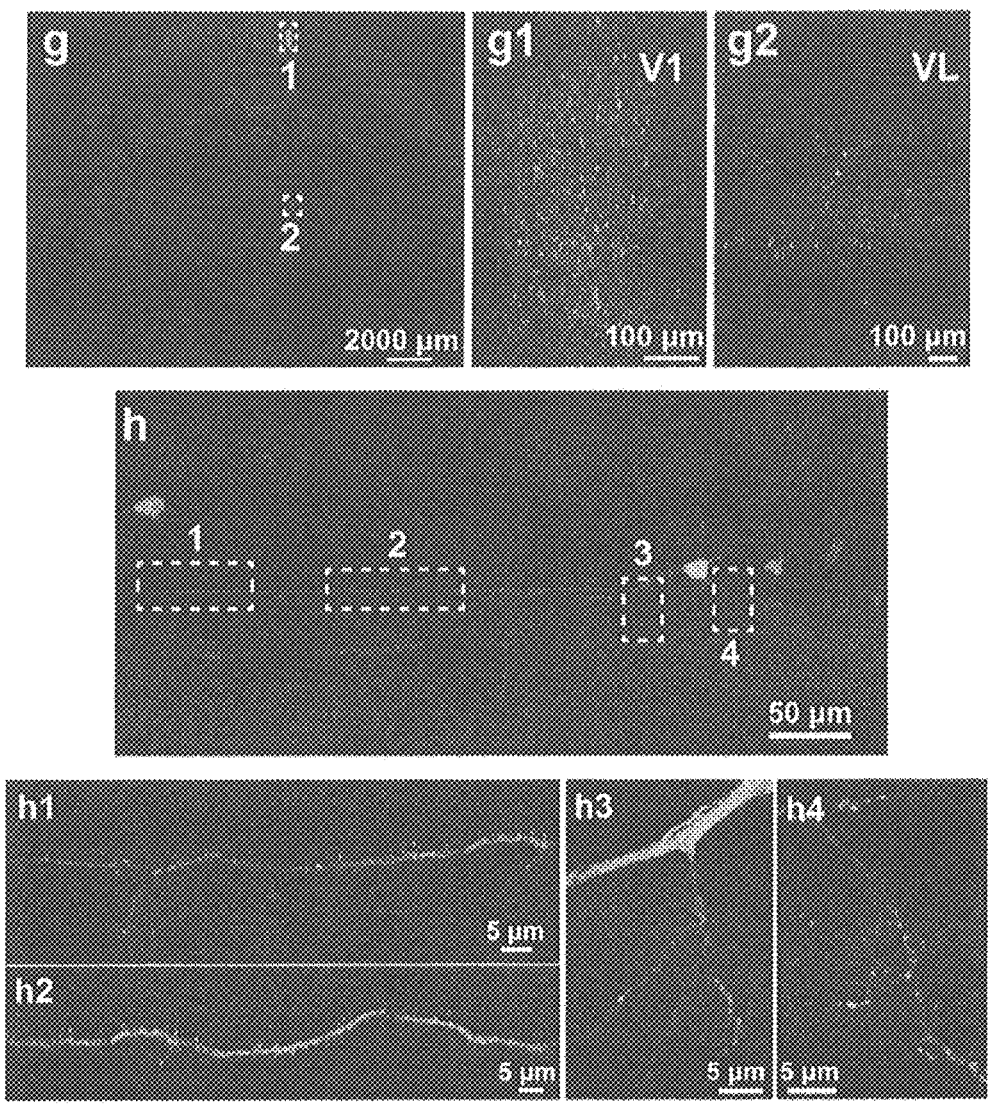

Referring now to FIG. 8, there is shown the mapping of the M1 projection output in tree shrew using H129-G4. (a) Comparison of mouse and tree shrew brains. The brains of adult mouse and tree shrew are imaged with top (left) or side view (middle) after perfusion, fixation and dehydration. (b-g) Tracing results of tree threw M1 projection output with H129-G4. H129-G4 ($2 \times 10^6$ pfu in 300 nl) were injected into the M1 of tree shrews together with CTB (red), and the brains were obtained at 6 dpi. Representative images of the coronal brain sections are shown, and the boxed regions are displayed with a higher magnification. (h) A representative H129-G4 labeled single neuron in tree threw. A representative GFP-labeled neuron around the injection is shown, and the magnified images of the apical (h1-h3) and basal dendrites (h4) are presented in the right.

The tree shrew (*Tupaia belangeri chinensis*), a smaller size prosimian primate, is much closer to the other primates than rodents at behavioral, anatomical, genomic, and evolutionary levels [26]. Its brain structures and neuronal circuits are also more similar to those of other primates than rodents. So far, no viral tracer has been reported to transneuronally map the neuronal circuits in the tree shrew. To test the applicability in tree shrews, H129-G4 was intracerebrally injected to M1 of the tree shrew brain together with CTB. Considering the larger size of the tree shrew brain than the mouse brain (FIG. 8(a)), the injected virus amount was increased to $2 \times 10^6$ pfu in 300 nl. At 6 dpi (FIG. 8(b)), both GFP and CTB labeled the injection site. Similar to the outputs of M1 in mice, GFP labeled cells were also observed in the contralateral M1, S1, CPu (FIG. 8(d)-(e)), and thalamus (FIG. 8(f)-(g)). Interestingly, injection of H129-G4 into the M1 of tree shrew brain resulted in GFP positive cells in the piriform cortex (Pir) (FIG. 8(c)), infraradiata dorsalis (IRd) (FIG. 8(c)-(d)), claustrum (Cl) and primary visual cortex (V1) (FIG. 8(g)), whereas the these brain regions were not labeled in mice. The labeling intensity of H129-G4 was lower in tree shrews than that in mice, but was still high enough to reveal the structure of single neurons (FIG. 8(h)), including the apical and basal dendrites.

14. Tracing the Visual Pathway Using H129-G4

Figure 9:
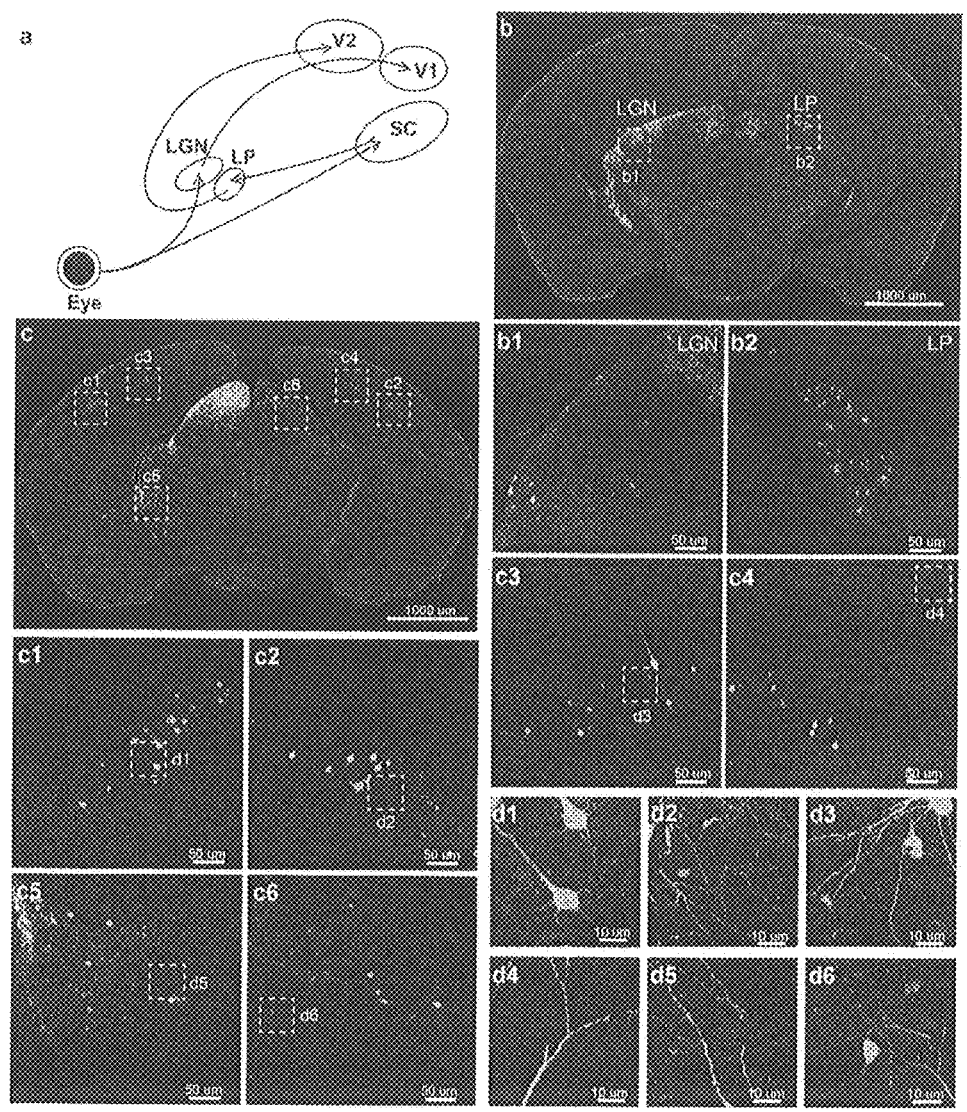
FIG. 9 shows the tracing the visual pathway using H129-G4.

Referring now to FIG. 9, there are shown the tracing the visual pathway using H129-G4; (a) Schema of the mouse visual pathway. LGN, lateral geniculate nucleus; LP, lateral posterior thalamic nucleus; SC, superior colliculus; V1 and V2, primary and secondary visual cortex; (b-d) Representative results of H129-G4 tracing the visual pathway. H129-G4 ($10^6$ pfu in 1 µl) were injected into the subretina of wild-type C57BL/6 mice, and images were obtained at 6 dpi. Representative images at LGN and LP (b) as well as visual cortex (c) are shown, and the boxed regions are magnified correspondingly.

15. Tracing the Olfactory Pathway Using H129-G4

Figure 10:
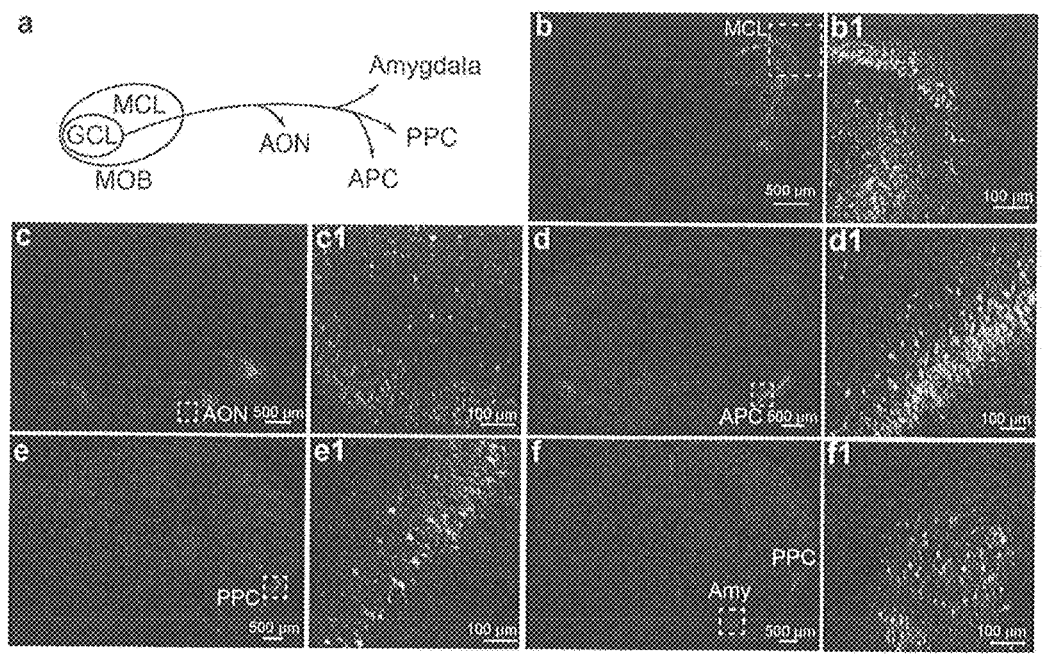
FIG. 10 shows the tracing the olfactory pathway using H129-G4.

Referring now to FIG. 10, there are shown the tracing the olfactory pathway using H129-G4; (a) Schema of the mouse olfactory pathway. MOB, main olfactory bulb; GCL, granule cell layer; MCL, mitral cell layer; AON, anterior olfactory nucleus; APC, anterior piriform cortex; PPC, posterior piriform cortex; (b-f) Representative results of H129-G4 tracing the olfactory pathway. H129-G4 ($10^6$ pfu in 200 nl) were injected into the GCL of wild-type C57BL/6 mice, and the images were taken at 4 dpi. The representative images of MOB (b), AON (c), APC (d), PPC (e) and Amy (f) are shown, and the boxed regions are magnified.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

REFERENCES

1. Nassi J J, Cepko C L, Born R T, Beier K T. 2015. Neuroanatomy goes viral! *Front Neuroanat* 9:80.
2. Beier K T, Saunders A B, Oldenburg I A, Sabatini B L, Cepko C L. 2013. Vesicular stomatitis virus with the rabies virus glycoprotein directs retrograde transsynaptic transport among neurons in vivo. *Front Neural Circuits* 7:11.
3. Beier K T, Saunders A, Oldenburg I A, Miyamichi K, Akhtar N, Luo L, Whelan S P, Sabatini B, Cepko C L. 2011. Anterograde or retrograde transsynaptic labeling of CNS neurons with vesicular stomatitis virus vectors. *Proc Natl Acad Sci USA* 108:15414-15419.
4. McGovern A E, Driessen A K, Simmoris D G, Powell J, Davis-Poynter N, Farrell M J, Mazzone S B. 2015. Distinct brainstem and forebrain circuits receiving tracheal sensory neuron inputs revealed using a novel conditional anterograde transsynaptic viral tracing system. *J Neurosci* 35:7041-7055.
5. Lo L, Anderson D J. 2011. A Cre-dependent, anterograde transsynaptic viral tracer for mapping output pathways of genetically marked neurons. *Neuron* 72:938-950.
6. Zemanick M C, Strick P L, Dix R D. 1991. Direction of transneuronal transport of herpes simplex virus 1 in the primate motor system is strain-dependent. *Proc Natl Acad Sci USA* 88:8048-8051.
7. LaVail J H, Topp K S, Giblin P A, Garner J A. 1997. Factors that contribute to the transneuronal spread of herpes simplex virus. *J Neurosci Res* 49:485-496.
8. Sun N, Cassell M D, Perlman S. 1996. Anterograde, transneuronal transport of herpes simplex virus type 1 strain H129 in the murine visual system. *J Virol* 70:5405-5413.
9. Barnett E M, Evans G D, Sun N, Perlman S, Cassell M D. 1995. Anterograde tracing of trigeminal afferent pathways from the murine tooth pulp to cortex using herpes simplex virus type 1. *J Neurosci* 15:2972-2984.
10. Rinaman L, Schwartz G. 2004. Anterograde transneuronal viral tracing of central viscerosensory pathways in rats. *Journal of Neuroscience* 24:2782-2786.
11. Kelly R M, Strick P L. 2003. Cerebellar loops with motor cortex and prefrontal cortex of a nonhuman primate. *J Neurosci* 23:8432-8444.
12. Archin N M, Atherton S S. 2002. Rapid spread of a neurovirulent strain of HSV-1 through the CNS of BALB/c mice following anterior chamber inoculation. *J Neurovirol* 8:122-135.
13. Beier K T, Mundell N A, Pan Y A, Cepko C L. 2016. Anterograde or Retrograde Transsynaptic Circuit Tracing in Vertebrates with Vesicular Stomatitis Virus Vectors. *Curr Protoc Neurosci* 74:1 26 21-21 26 27.
14. McGovern A E, Davis-Poynter N, Rakoczy J, Phipps S, Simmons D G, Mazzone S B. 2012. Anterograde neuronal circuit tracing using a genetically modified herpes simplex virus expressing EGFP. *J Neurosci Methods* 209:158-167.
15. Wadsworth S, Jacob R J, Roizman B. 1975. Anatomy of herpes simplex virus DNA. II. Size, composition, and arrangement of inverted terminal repetitions. *J Virol* 15:1487-1497.
16. Delius H, Clements J B. 1976. A partial denaturation map of herpes simplex virus type 1 DNA: evidence for inversions of the unique DNA regions. *J Gen Virol* 33:125-133.
17. He B, Chou J, Brandimarti R, Mohr I, Gluzman Y, Roizman B. 1997. Suppression of the phenotype of gamma(1)34.5-herpes simplex virus 1: failure of activated RNA-dependent protein kinase to shut off protein synthesis is associated with a deletion in the domain of the alpha47 gene. *J Virol* 71:6049-6054.
18. Wagner M, Jonjic S, Koszinowski U H, Messerle M. 1999. Systematic excision of vector sequences from the BAC-cloned herpesvirus genome during virus reconstitution. *J Virol* 73:7056-7060.
19. Messerle M, Crnkovic I, Hammerschmidt W, Ziegler H, Koszinowski U H. 1997. Cloning and mutagenesis of a herpesvirus genome as an infectious bacterial artificial chromosome. *Proc Natl Acad Sci USA* 94:14759-14763.
20. Seibenhener M L, Wooten M W. 2012. Isolation and culture of hippocampal neurons from prenatal mice. *J Vis Exp* doi:10.3791/3634.
21. Park J W, Vahidi B, Taylor A M, Rhee S W, Jeon N L. 2006. Microfluidic culture platform for neuroscience research. *Nat Protoc* 1:2128-2136.
22. Szpara M L, Parsons L, Enquist L W. 2010. Sequence variability in clinical and laboratory isolates of herpes simplex virus 1 reveals new mutations. *J Virol* 84:5303-5313.
23. Taylor A M, Blurton-Jones M, Rhee S W, Cribbs D H, Cotman C W, Jeon N L. 2005. A microfluidic culture platform for CNS axonal injury, regeneration and transport. *Nature Methods* 2:599-605.
24. Harris J, Lee H, Vahidi B, Tu C, Cribbs D, Jeon N L, Cotman C. 2007. Fabrication of a Microfluidic Device for the Compartmentalization of Neuron Soma and Axons. doi:doi:10.3791/261:e261.
25. Paxinos G, Franklin K B J. 2003. The Mouse Brain in Stereotaxic Coordinates. Academic Press.
26. Zhou J-N, Ni R-J. 2017. The Tree Shrew (*Tupaia belangeri chinensis*) Brain in Stereotaxic Coordinates. Springer Singapore.
27. Xiong H, Zhou Z, Zhu M, Lv X, Li A, Li S, Li L, Yang T, Wang S, Yang Z, Xu T, Luo Q, Gong H, Zeng S. 2014. Chemical reactivation of quenched fluorescent protein molecules enables resin-embedded fluorescence microimaging. Nat Commun 5:3992.
28. Zheng T, Yang Z, Li A, Lv X, Zhou Z, Wang X, Qi X, Li S, Luo Q, Gong H, Zeng S. 2013. Visualization of brain circuits using two-photon fluorescence micro-optical sectioning tomography. Opt Express 21:9839-9850.
29. Gong H, Zeng S Q, Yan C, Lv X H, Yang Z Q, Xu T H, Feng Z, Ding W X, Qi X L, Li A A, Wu J P, Luo Q M. 2013. Continuously tracing brain-wide long-distance axonal projections in mice at a one-micron voxel resolution. Neuroimage 74:87-98.
30. Quan T, Zhou H, Li J, Li S, Li A, Li Y, Lv X, Luo Q, Gong H, Zeng S. 2016. NeuroGPS-Tree: automatic reconstruction of large-scale neuronal populations with dense neurites. Nat Methods 13:51-54.
31. Fan Y, Huang Z Y, Cao C C, Chen C S, Chen Y X, Fan D D, He J, Hou H L, Hu L, Hu X T, Jiang X T, Lai R, Lang Y S, Liang B, Liao S G, Mu D, Ma Y Y, Niu Y Y, Sun X Q, Xia J Q, Xiao J, Xiong Z Q, Xu L, Yang L, Zhang Y, Zhao W, Zhao X D, Zheng Y T, Zhou J M, Zhu Y B, Zhang O J, Wang J, Yao Y G. 2013. Genome of the Chinese tree shrew. Nat Commun 4:1426.
32. Li L, Li Z, Wang E, Yang R, Xiao Y, Han H, Lang F, Li X, Xia Y, Gao F, Li Q, Fraser N W, Zhou J. 2015. Herpes Simplex Virus 1 Infection of Tree Shrews Differs from That of Mice in the Severity of Acute Infection and Viral Transcription in the Peripheral Nervous System. J Virol 90:790-804.

What is claimed is:

1. A recombinant Herpes Simplex Virus type 1 (HSV-1) strain H129-derived anterograde multi-synaptic transneuronal viral tracer for multi-synaptic neural circuit mapping, comprising:
   two or more fluorescence expression cassettes being integrated into the H129 genome at different locations;
   wherein each fluorescence expression cassette contains at least two copies of fluorescent protein-encoding sequences that are arranged in tandem, and at least one linker-encoding sequence, where at least one linker-encoding sequence is disposed between two fluorescent protein-encoding sequences, allowing transcription of fluorescent protein-encoding sequences and linker-encoding sequence as a single transcript;
   wherein for the at least two copies of fluorescent protein-encoding sequences in each fluorescent expression cassette, one encodes a membrane-bound fluorescent protein (mFP), and other encodes a fluorescent protein (FP) that is not membrane-bound, and the mFP and FP emit the same fluorescence;
   wherein the linker-encoding sequence encodes a linker peptide containing at least two adjacent amino acids that are highly inefficient in forming a peptide bond between them; thereby, when the single transcript is translated, the mFP and FP are stoichiometrically generated due to the impedence of peptide bond formation by the linker peptide; and
   wherein the at least two adjacent amino acids of the linker peptide are glycine and proline.

2. The recombinant H129-derived anterograde multi-synaptic transneuronal viral tracer of claim 1, wherein the fluorescence expression cassette further comprises a promoter, wherein the promoter controls transcription of the fluorescent protein-encoding constructs and linker-encoding sequence.

3. The recombinant H129-derived anterograde multi-synaptic transneuronal viral tracer of claim 2, wherein the promoter is operable in neuronal cells and selected from the group consisting of Cytomegalovirus (CMV) promoter, Simian virus 40 (SV40) promoter, Human cytomegalovirus immediate early/chicken β-actin promotor (CAG) promoter, elongation factor 1-alpha (EF1a) promoter, tyrosine hydroxylase (TH) promoter, and synapsin 1 (Syn1) promoter.

4. The recombinant H129-derived anterograde multi-synaptic transneuronal viral tracer of claim 1, wherein the fluorescent protein-encoding sequence encodes a green fluorescence protein (GFP) represented by an amino acid sequence of SEQ ID NO 2 or a variant thereof.

5. The recombinant H129-derived anterograde multi-synaptic transneuronal viral tracer of claim 1, wherein the fluorescent protein-encoding sequence encodes a membrane-bound green fluorescence protein (mGFP) represented by an amino acid sequence of SEQ ID NO 4 or a variant thereof.

6. The recombinant H129-derived anterograde multi-synaptic transneuronal viral tracer of claim 1, wherein the linker-encoding sequence encodes a linker peptide represented by an amino acid sequence of SEQ ID NO 6 or a variant thereof.

7. The recombinant H129-derived anterograde multi-synaptic transneuronal viral tracer of claim 1, wherein the fluorescent protein-encoding sequence and linker-encoding sequence encode a peptide represented by an amino acid sequence of SEQ ID NO 8 or variant with at least 98% identity thereof.

8. The recombinant H129-derived anterograde multi-synaptic transneuronal viral tracer of claim 1, further comprises a bacterial artificial chromosome (BAC) sequence.

* * * * *

SEQUENCE LISTING

<160> NUMBER OF SEQ ID NOS: 60

<210> SEQ ID NO 1
<211> LENGTH: 720
<212> TYPE: DNA

<213> ORGANISM: Artificial Sequence
<220> FEATURE:
<223> OTHER INFORMATION: Green fluorescence protein

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact cttcaagtc cgccatgccc gaaggctacg tccaggagcg caccatcttc      300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 2
<211> LENGTH: 239
<212> TYPE: PRT
<213> ORGANISM: Artificial Sequence
<220> FEATURE:
<223> OTHER INFORMATION: Green fluorescence protein

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205
```

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 3
<211> LENGTH: 780
<212> TYPE: DNA
<213> ORGANISM: Artificial Sequence
<220> FEATURE:
<223> OTHER INFORMATION: modified green fluorescence protein

<400> SEQUENCE: 3
atgctgtgct gtatgagaag aaccaaacag gttgaaaaga atgatgagga ccaaaagatc      60
atggtgagca agggcgagga gctgttcacc ggggtggtgc ccatcctggt cgagctggac     120
ggcgacgtaa acggccacaa gttcagcgtg tccggcgagg gcgagggcga tgccacctac     180
ggcaagctga ccctgaagtt catctgcacc accggcaagc tgcccgtgcc ctggcccacc     240
ctcgtgacca ccctgaccta cggcgtgcag tgcttcagcc gctaccccga ccacatgaag     300
cagcacgact tcttcaagtc cgccatgccc gaaggctacg tccaggagcg caccatcttc     360
ttcaaggacg acggcaacta caagacccgc gccgaggtga agttcgaggg cgacaccctg     420
gtgaaccgca tcgagctgaa gggcatcgac ttcaaggagg acggcaacat cctggggcac     480
aagctggagt acaactacaa cagccacaac gtctatatca tggccgacaa gcagaagaac     540
ggcatcaagg tgaacttcaa gatccgccac aacatcgagg acggcagcgt gcagctcgcc     600
gaccactacc agcagaacac ccccatcggc gacggccccg tgctgctgcc cgacaaccac     660
tacctgagca cccagtccgc cctgagcaaa gaccccaacg agaagcgcga tcacatggtc     720
ctgctggagt tcgtgaccgc cgccgggatc actctcggca tggacgagct gtacaagtaa     780

<210> SEQ ID NO 4
<211> LENGTH: 259
<212> TYPE: PRT
<213> ORGANISM: Artificial Sequence
<220> FEATURE:
<223> OTHER INFORMATION: modified green fluorescence protein

<400> SEQUENCE: 4

Met Leu Cys Cys Met Arg Arg Thr Lys Gln Val Glu Lys Asn Asp Glu
1               5                   10                  15

Asp Gln Lys Ile Met Val Ser Lys Gly Glu Glu Leu Phe Thr Gly Val
                20                  25                  30

Val Pro Ile Leu Val Glu Leu Asp Gly Asp Val Asn Gly His Lys Phe
            35                  40                  45

Ser Val Ser Gly Glu Gly Glu Gly Asp Ala Thr Tyr Gly Lys Leu Thr
        50                  55                  60

Leu Lys Phe Ile Cys Thr Thr Gly Lys Leu Pro Val Pro Trp Pro Thr
65                  70                  75                  80

Leu Val Thr Thr Leu Thr Tyr Gly Val Gln Cys Phe Ser Arg Tyr Pro
                85                  90                  95

Asp His Met Lys Gln His Asp Phe Phe Lys Ser Ala Met Pro Glu Gly
            100                 105                 110

Tyr Val Gln Glu Arg Thr Ile Phe Phe Lys Asp Asp Gly Asn Tyr Lys
        115                 120                 125

Thr Arg Ala Glu Val Lys Phe Glu Gly Asp Thr Leu Val Asn Arg Ile
    130                 135                 140

```
Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
            165                 170                 175

Lys Gln Lys Asn Gly Ile Lys Val Asn Phe Lys Ile Arg His Asn Ile
        180                 185                 190

Glu Asp Gly Ser Val Gln Leu Ala Asp His Tyr Gln Gln Asn Thr Pro
    195                 200                 205

Ile Gly Asp Gly Pro Val Leu Leu Pro Asp Asn His Tyr Leu Ser Thr
210                 215                 220

Gln Ser Ala Leu Ser Lys Asp Pro Asn Glu Lys Arg Asp His Met Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 5
<211> LENGTH: 54
<212> TYPE: DNA
<213> ORGANISM: Artificial Sequence
<220> FEATURE:
<223> OTHER INFORMATION: linker sequence

<400> SEQUENCE: 5
gagggcagag gaagtctgct aacatgcggt gacgtcgagg agaatcctgg ccca        54

<210> SEQ ID NO 6
<211> LENGTH: 18
<212> TYPE: PRT
<213> ORGANISM: Artificial Sequence
<220> FEATURE:
<223> OTHER INFORMATION: linker sequence

<400> SEQUENCE: 6

Glu Gly Arg Gly Ser Leu Leu Thr Cys Gly Asp Val Glu Glu Asn Pro
1               5                   10                  15

Gly Pro

<210> SEQ ID NO 7
<211> LENGTH: 1548
<212> TYPE: DNA
<213> ORGANISM: Artificial Sequence
<220> FEATURE:
<223> OTHER INFORMATION: mGFP-2A-GFP sequence

<400> SEQUENCE: 7
atgctgtgct gtatgagaag aaccaaacag gttgaaaaga atgatgagga ccaaaagatc     60
atggtgagca agggcgagga gctgttcacc ggggtggtgc ccatcctggt cgagctggac    120
ggcgacgtaa acggccacaa gttcagcgtg tccggcgagg gcgagggcga tgccacctac    180
ggcaagctga ccctgaagtt catctgcacc accggcaagc tgcccgtgcc ctggcccacc    240
ctcgtgacca ccctgaccta cggcgtgcag tgcttcagcc gctaccccga ccacatgaag    300
cagcacgact tcttcaagtc cgccatgccc gaaggctacg tccaggagcg caccatcttc    360
ttcaaggacg acggcaacta caagacccgc gccgaggtga agttcgaggg cgacaccctg    420
gtgaaccgca tcgagctgaa gggcatcgac ttcaaggagg acggcaacat cctggggcac    480
aagctggagt acaactacaa cagccacaac gtctatatca tggccgacaa gcagaagaac    540
ggcatcaagg tgaacttcaa gatccgccac aacatcgagg acggcagcgt gcagctcgcc    600
```

```
gaccactacc agcagaacac ccccatcggc gacggccccg tgctgctgcc cgacaaccac    660
tacctgagca cccagtccgc cctgagcaaa gaccccaacg agaagcgcga tcacatggtc    720
ctgctggagt tcgtgaccgc cgccgggatc actctcggca tggacgagct gtacaaggag    780
ggcagaggaa gtctgctaac atgcggtgac gtcgaggaga tcctggccc  agtgagcaag    840 ggcgaggagc tgttcaccgg ggtggtgccc atcctggtcg agctggacgg cgacgtaaac    900
ggccacaagt tcagcgtgtc cggcgagggc gagggcgatg ccacctacgg caagctgacc    960
ctgaagttca tctgcaccac cggcaagctg cccgtgccct ggcccaccct cgtgaccacc   1020
ctgacctacg gcgtgcagtg cttcagccgc taccccgacc acatgaagca gcacgacttc   1080
ttcaagtccg ccatgcccga aggctacgtc caggagcgca ccatcttctt caaggacgac   1140
ggcaactaca agacccgcgc cgaggtgaag ttcgagggcg acaccctggt gaaccgcatc   1200
gagctgaagg gcatcgactt caaggaggac ggcaacatcc tggggcacaa gctggagtac   1260
aactacaaca gccacaacgt ctatatcatg gccgacaagc agaagaacgg catcaaggtg   1320
aacttcaaga tccgccacaa catcgaggac ggcagcgtgc agctcgccga ccactaccag   1380
cagaacaccc ccatcggcga cggccccgtg ctgctgcccg acaaccacta cctgagcacc   1440
cagtccgccc tgagcaaaga ccccaacgag aagcgcgatc acatggtcct gctggagttc   1500
gtgaccgccg ccgggatcac tctcggcatg gacgagctgt acaagtaa              1548

<210> SEQ ID NO 8
<211> LENGTH: 515
<212> TYPE: PRT
<213> ORGANISM: Artificial Sequence
<220> FEATURE:
<223> OTHER INFORMATION: mGFP-2A-GFP sequence

<400> SEQUENCE: 8

Met Leu Cys Cys Met Arg Arg Thr Lys Gln Val Glu Lys Asn Asp Glu
1               5                   10                  15

Asp Gln Lys Ile Met Val Ser Lys Gly Glu Glu Leu Phe Thr Gly Val
                20                  25                  30

Val Pro Ile Leu Val Glu Leu Asp Gly Asp Val Asn Gly His Lys Phe
            35                  40                  45

Ser Val Ser Gly Glu Gly Glu Gly Asp Ala Thr Tyr Gly Lys Leu Thr
        50                  55                  60

Leu Lys Phe Ile Cys Thr Thr Gly Lys Leu Pro Val Pro Trp Pro Thr
65                  70                  75                  80

Leu Val Thr Thr Leu Thr Tyr Gly Val Gln Cys Phe Ser Arg Tyr Pro
                85                  90                  95

Asp His Met Lys Gln His Asp Phe Phe Lys Ser Ala Met Pro Glu Gly
                100                 105                 110

Tyr Val Gln Glu Arg Thr Ile Phe Phe Lys Asp Asp Gly Asn Tyr Lys
            115                 120                 125

Thr Arg Ala Glu Val Lys Phe Glu Gly Asp Thr Leu Val Asn Arg Ile
        130                 135                 140

Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
                165                 170                 175

Lys Gln Lys Asn Gly Ile Lys Val Asn Phe Lys Ile Arg His Asn Ile
                180                 185                 190
```

```
Glu Asp Gly Ser Val Gln Leu Ala Asp His Tyr Gln Gln Asn Thr Pro
            195                 200                 205
Ile Gly Asp Gly Pro Val Leu Leu Pro Asp Asn His Tyr Leu Ser Thr
210                 215                 220
Gln Ser Ala Leu Ser Lys Asp Pro Asn Glu Lys Arg Asp His Met Val
225                 230                 235                 240
Leu Leu Glu Phe Val Thr Ala Ala Gly Ile Thr Leu Gly Met Asp Glu
                245                 250                 255
Leu Tyr Lys Glu Gly Arg Gly Ser Leu Leu Thr Cys Gly Asp Val Glu
            260                 265                 270
Glu Asn Pro Gly Pro Val Ser Lys Gly Glu Glu Leu Phe Thr Gly Val
            275                 280                 285
Val Pro Ile Leu Val Glu Leu Asp Gly Asp Val Asn Gly His Lys Phe
290                 295                 300
Ser Val Ser Gly Glu Gly Glu Gly Asp Ala Thr Tyr Gly Lys Leu Thr
305                 310                 315                 320
Leu Lys Phe Ile Cys Thr Thr Gly Lys Leu Pro Val Pro Trp Pro Thr
                325                 330                 335
Leu Val Thr Thr Leu Thr Tyr Gly Val Gln Cys Phe Ser Arg Tyr Pro
            340                 345                 350
Asp His Met Lys Gln His Asp Phe Phe Lys Ser Ala Met Pro Glu Gly
            355                 360                 365
Tyr Val Gln Glu Arg Thr Ile Phe Phe Lys Asp Asp Gly Asn Tyr Lys
            370                 375                 380
Thr Arg Ala Glu Val Lys Phe Glu Gly Asp Thr Leu Val Asn Arg Ile
385                 390                 395                 400
Glu Leu Lys Gly Ile Asp Phe Lys Glu Asp Gly Asn Ile Leu Gly His
                405                 410                 415
Lys Leu Glu Tyr Asn Tyr Asn Ser His Asn Val Tyr Ile Met Ala Asp
            420                 425                 430
Lys Gln Lys Asn Gly Ile Lys Val Asn Phe Lys Ile Arg His Asn Ile
            435                 440                 445
Glu Asp Gly Ser Val Gln Leu Ala Asp His Tyr Gln Gln Asn Thr Pro
450                 455                 460
Ile Gly Asp Gly Pro Val Leu Leu Pro Asp Asn His Tyr Leu Ser Thr
465                 470                 475                 480
Gln Ser Ala Leu Ser Lys Asp Pro Asn Glu Lys Arg Asp His Met Val
                485                 490                 495
Leu Leu Glu Phe Val Thr Ala Ala Gly Ile Thr Leu Gly Met Asp Glu
            500                 505                 510
Leu Tyr Lys
        515
```

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cgggatccag actgacacat taaaaaacac                                      30

<210> SEQ ID NO 10
<211> LENGTH: 65
<212> TYPE: DNA

<213> ORGANISM: Artificial Sequence
<220> FEATURE:
<223> OTHER INFORMATION: primer

<400> SEQUENCE: 10
cccaagctta taacttcgta taatgtatgc tatacgaagt tataacacgg aaggagacaa    60
taccg                                                                65

<210> SEQ ID NO 11
<211> LENGTH: 64
<212> TYPE: DNA
<213> ORGANISM: Artificial Sequence
<220> FEATURE:
<223> OTHER INFORMATION: primer

<400> SEQUENCE: 11
cccaagctta taacttcgta taatgtatgc tatacgaagt tattcagtta gcctccccca    60
tctc                                                                 64

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
cgggatccct tcggacctcg cgggggccgc                                     30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
cgggatccag actgacacat taaaaaacac                                     30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
cgggatccct tcggacctcg cgggggccgc                                     30

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
tcggtttgaa aggcatcg                                                  18

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
gacaaggtcg ccatctgct                                                      19

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gggcacgcga gactatcaga g                                                   21

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
tcattcgcca tcgggatagt c                                                   21

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
atggaggagc ccctaccaga                                                     20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
taccaaagac cggggcgaat                                                     20

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
tggtaactag ttaacggcaa gtccg                                               25

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
atgccgggac ttaagtggcc gtata                                               25

<210> SEQ ID NO 23

```
<211> LENGTH: 24
<212> TYPE: DNA
<213> ORGANISM: Artificial Sequence
<220> FEATURE:
<223> OTHER INFORMATION: primer

<400> SEQUENCE: 23
atgaagacca atccgctacc cgca                                           24

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
aacactcgcg tttcgggttt cagt                                           24

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
atgagtcagt ggggatccgg                                                20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
cccggaacga accccaagct                                                20

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
gccaacgacc acatccct                                                  18

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
cagcggcaaa caaagcag                                                  18

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
```
ggggtttctt ctcggtgttt g                                        21

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gcggtgctga tggtaatgtg                                          20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
aaattgccct agcacagggg                                          20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
ggtctctccg gcgcacataa                                          20

<210> SEQ ID NO 33
<211> LENGTH: 29
<212> TYPE: DNA
<213> ORGANISM: Artificial Sequence
<220> FEATURE:
<223> OTHER INFORMATION: primer

<400> SEQUENCE: 33
cgggatccca agtttcgagg tcgagtgtc                                29

<210> SEQ ID NO 34
<211> LENGTH: 28
<212> TYPE: DNA
<213> ORGANISM: Artificial Sequence
<220> FEATURE:
<223> OTHER INFORMATION: primer

<400> SEQUENCE: 34
gcgaattcgg aacggaccgt gttgacaa                                 28

<210> SEQ ID NO 35
<211> LENGTH: 28
<212> TYPE: DNA
<213> ORGANISM: Artificial Sequence
<220> FEATURE:
<223> OTHER INFORMATION: primer

<400> SEQUENCE: 35
gcgtcgacat gctgtgctgt atgagaag                                 28

<210> SEQ ID NO 36
<211> LENGTH: 27
<212> TYPE: DNA

```
<213> ORGANISM: Artificial Sequence
<220> FEATURE:
<223> OTHER INFORMATION: primer

<400> SEQUENCE: 36 cgggatccttt acttgtacag ctcgtcc                                          27

<210> SEQ ID NO 37
<211> LENGTH: 78
<212> TYPE: DNA
<213> ORGANISM: Artificial Sequence
<220> FEATURE:
<223> OTHER INFORMATION: primer

<400> SEQUENCE: 37
caaagaatgg atgggaggag ttcaggaagc cggggagagg gcccgcggcg acattgatta      60
ttgactagtt attaatag                                                    78

<210> SEQ ID NO 38
<211> LENGTH: 76
<212> TYPE: DNA
<213> ORGANISM: Artificial Sequence
<220> FEATURE:
<223> OTHER INFORMATION: primer

<400> SEQUENCE: 38
ccgcaccaac ccgccagaag agccaaagtc aacacaacaa cgccttaaat gaggcggccg      60
cactagtgat agatct                                                      76

<210> SEQ ID NO 39
<211> LENGTH: 78
<212> TYPE: DNA
<213> ORGANISM: Artificial Sequence
<220> FEATURE:
<223> OTHER INFORMATION: primer

<400> SEQUENCE: 39
cgaccgtggt gtatgtctgg tgtgtggcgt ccgatcccgt tactatcacc acattgatta      60
ttgactagtt attaatag                                                    78

<210> SEQ ID NO 40
<211> LENGTH: 77
<212> TYPE: DNA
<213> ORGANISM: Artificial Sequence
<220> FEATURE:
<223> OTHER INFORMATION: primer

<400> SEQUENCE: 40
cgtgtcgttt ttaaaaaacc cacaatcgcc ggggttgagg ggggggggac gttcaggtgg      60
cacttttcgg ggaaatg                                                     77

<210> SEQ ID NO 41
<211> LENGTH: 77
<212> TYPE: DNA
<213> ORGANISM: Artificial Sequence
<220> FEATURE:
<223> OTHER INFORMATION: primer

<400> SEQUENCE: 41
tttattgccg tcatagcgcg ggttccttcc ggtattgtct ccttccgtgt tcgctcagaa      60
gaactcgtca agaaggc                                                     77
```

```
<210> SEQ ID NO 42
<211> LENGTH: 76
<212> TYPE: DNA
<213> ORGANISM: Artificial Sequence
<220> FEATURE:
<223> OTHER INFORMATION: primer

<400> SEQUENCE: 42
cgggcgtatt ttttgagtta tcgagatttt caggagctaa ggaagctaaa atgattgaac    60
aagatggatt gcacgc                                                   76

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
caacacccgt gcgttttatt c                                             21

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
gtaagaggtt ccaactttca cc                                            22

<210> SEQ ID NO 45
<211> LENGTH: 29
<212> TYPE: DNA
<213> ORGANISM: Artificial Sequence
<220> FEATURE:
<223> OTHER INFORMATION: primer

<400> SEQUENCE: 45
cgggatccca agtttcgagg tcgagtgtc                                     29

<210> SEQ ID NO 46
<211> LENGTH: 28
<212> TYPE: DNA
<213> ORGANISM: Artificial Sequence
<220> FEATURE:
<223> OTHER INFORMATION: primer

<400> SEQUENCE: 46
gcgaattcgg aacggaccgt gttgacaa                                      28

<210> SEQ ID NO 47
<211> LENGTH: 29
<212> TYPE: DNA
<213> ORGANISM: Artificial Sequence
<220> FEATURE:
<223> OTHER INFORMATION: primer

<400> SEQUENCE: 47
cccaagctta tgctgtgctg tatgagaag                                     29

<210> SEQ ID NO 48
<211> LENGTH: 78
<212> TYPE: DNA
<213> ORGANISM: Artificial Sequence
<220> FEATURE:
```

<223> OTHER INFORMATION: primer

<400> SEQUENCE: 48
cggtcgactg ggccaggatt ctcctcgacg tcaccgcatg ttagcagact tcctctgccc  60
tccttgtaca gctcgtcc  78

<210> SEQ ID NO 49
<211> LENGTH: 78
<212> TYPE: DNA
<213> ORGANISM: Artificial Sequence
<220> FEATURE:
<223> OTHER INFORMATION: primer

<400> SEQUENCE: 49
aggtaccttc tgaggcggaa agaaccagct gtggaatgtg tgtcagttag acattgatta  60
ttgactagtt attaatag  78

<210> SEQ ID NO 50
<211> LENGTH: 76
<212> TYPE: DNA
<213> ORGANISM: Artificial Sequence
<220> FEATURE:
<223> OTHER INFORMATION: primer

<400> SEQUENCE: 50
tctgcgacct ggcgcgcacg tttgcccggg agatggggga ggctaactga ggaacggacc  60
gtgttgacaa ttaatc  76

<210> SEQ ID NO 51
<211> LENGTH: 21
<212> TYPE: DNA
<213> ORGANISM: Artificial Sequence
<220> FEATURE:
<223> OTHER INFORMATION: primer

<400> SEQUENCE: 51
acctctgaaa gaggaacttg g  21

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
gatggtccag acccacgtca c  21

<210> SEQ ID NO 53
<211> LENGTH: 29
<212> TYPE: DNA
<213> ORGANISM: Artificial Sequence
<220> FEATURE:
<223> OTHER INFORMATION: primer

<400> SEQUENCE: 53
cgggatcctg atcggcacgt aagaggttc  29

<210> SEQ ID NO 54
<211> LENGTH: 31
<212> TYPE: DNA
<213> ORGANISM: Artificial Sequence
<220> FEATURE:
<223> OTHER INFORMATION: primer

```
<400> SEQUENCE: 54
cgggatcctt acgccccgcc ctgccactca t                                      31

<210> SEQ ID NO 55
<211> LENGTH: 78
<212> TYPE: DNA
<213> ORGANISM: Artificial Sequence
<220> FEATURE:
<223> OTHER INFORMATION: primer

<400> SEQUENCE: 55
caaagaatgg atgggaggag ttcaggaagc cggggagagg gcccgcggcg acattgatta       60
ttgactagtt attaatag                                                     78

<210> SEQ ID NO 56
<211> LENGTH: 76
<212> TYPE: DNA
<213> ORGANISM: Artificial Sequence
<220> FEATURE:
<223> OTHER INFORMATION: primer

<400> SEQUENCE: 56
ccgcaccaac ccgccagaag agccaaagtc aacacaacaa cgccttaaat gtgatcggca       60
cgtaagaggt tccaac                                                       76

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
cggaaaccaa agaaggaagc                                                   20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gggagcccaa caaacagcac                                                   20

<210> SEQ ID NO 59
<211> LENGTH: 9193
<212> TYPE: DNA
<213> ORGANISM: Artificial Sequence
<220> FEATURE:
<223> OTHER INFORMATION: pUS-F5

<400> SEQUENCE: 59
aagcttttat ctaatctccc agcgtggttt aatcagacga tcgaaaattt cattgcagac       60
aggttcccaa atagaaagag catttctcca ggcaccagtt gaagagcgtt gatcaatggc      120
ctgttcaaaa acagttctca tccggatctg acctttacca acttcatccg tttcacgtac      180
aacatttttt agaaccatgc ttccccaggc atcccgaatt tgctcctcca tccacgggga      240
ctgagagcca ttactattgc tgtatttggt aagcaaaata cgtacatcag gctcgaaccc      300
tttaagatca acgttcttga gcagatcacg aagcatatcg aaaaactgca gtgcggaggt      360
```

```
gtagtcaaac aactcagcag gcgtgggaac aatcagcaca tcagcagcac atacgacatt      420
aatcgtgccg atacccaggt taggcgcgct gtcaataact atgacatcat agtcatgagc      480
aacagtttca atggccagtc ggagcatcag gtgtggatcg gtgggcagtt taccttcatc      540
aaatttgccc attaactcag tttcaatacg gtgcagagcc agacaggaag gaataatgtc      600
aagccccggc cagcaagtgg gctttattgc ataagtgaca tcgtcctttt ccccaagata      660
gaaaggcagg agagtgtctt ctgcatgaat atgaagatct ggtacccatc cgtgatacat      720
tgaggctgtt ccctgggggt cgttaccttc cacgagcaaa acacgtagcc ccttcagagc      780
cagatcctga gcaagatgaa cagaaactga ggttttgtaa acgccacctt tatgggcagc      840
aaccccgatc accggtggaa atacgtcttc agcacgtcgc aatcgcgtac caaacacatc      900
acgcatatga ttaatttgtt caattgtata accaacacgt tgctcaaccc gtcctcgaat      960
ttccatatcc gggtgcggta gtcgccctgc tttctcggca tctctgatag cctgagaaga     1020
aaccccaact aaatccgctg cttcacctat tctccagcgc cgggttattt tcctcgcttc     1080
cgggctgtca tcattaaact gtgcaatggc gatagccttc gtcatttcat gaccagcgtt     1140
tatgcactgg ttaagtgttt ccatgagttt cattctgaac atcctttaat cattgctttg     1200 cgtttttta ttaaatcttg caatttactg caaagcaaca acaaaatcgc aaagtcatca     1260
aaaaaccgca aagttgttta aaataagagc aacactacaa aaggagataa gaagagcaca     1320
tacctcagtc acttattatc actagcgctc gccgcagccg tgtaaccgag catagcgagc     1380
gaactggcga ggaagcaaag aagaactgtt ctgtcagata gctcttacgc tcagcgcaag     1440
aagaaatatc caccgtggga aaaactccag gtagaggtac acacgcggat agccaattca     1500
gagtaataaa ctgtgataat caaccctcat caatgatgac gaactaaccc ccgatatcag     1560
gtcacatgac gaagggaaag agaaggaaat caactgtgac aaactgccct caaatttggc     1620
ttccttaaaa attacagttc aaaagtatg agaaaatcca tgcaggctga aggaaacagc     1680
aaaactgtga caaattaccc tcagtaggtc agaacaaatg tgacgaacca ccctcaaatc     1740
tgtgacagat aaccctcaga ctatcctgtc gtcatggaag tgatatcgcg aaggaaaat     1800 acgatatgag tcgtctggcg gcctttcttt ttctcaatgt atgagaggcg cattggagtt     1860
ctgctgttga tctcattaac acagacctgc aggaagcggc ggcggaagtc aggcatacgc     1920
tggtaacttt gaggcagctg gtaacgctct atgatccagt cgattttcag agagacgatg     1980
cctgagccat ccggcttacg atactgacac agggattcgt ataaacgcat ggcatacgga     2040
ttggtgattt cttttgtttc actaagccga aactgcgtaa accggttctg taacccgata     2100
aagaagggaa tgagatatgg gttgatatgt acactgtaaa gccctctgga tggactgtgc     2160
gcacgtttga taaccaagg aaaagattca tagccttttt catcgccggc atcctcttca     2220
gggcgataaa aaaccacttc cttccccgcg aaactcttca atgcctgccg tatatcctta     2280
ctggcttccg cagaggtcaa tccgaatatt tcagcatatt tagcaacatg gatctcgcag     2340
ataccgtcat gttcctgtag ggtgccatca gatttttctga tctggtcaac gaacagatac     2400
agcatacgtt tttgatcccg ggagagacta tatgccgcct cagtgaggtc gtttgactgg     2460
acgattcgcg ggctatttt acgtttcttg tgattgataa ccgctgtttc cgccatgaca     2520
gatccatgtg aagtgtgaca agtttttaga ttgtcacact aaataaaaaa gagtcaataa     2580
gcagggataa cttttgtgaa aaacagcttc ttctgagggc aatttgtcac agggttaagg     2640
gcaatttgtc acagacagga ctgtcatttg agggtgattt gtcacactga aagggcaatt     2700
tgtcacaaca ccttctctag aaccagcatg gataaaggcc tacaaggcgc tctaaaaaag     2760
```

```
aagatctaaa aactataaaa aaaataatta taaaaatatc cccgtggata agtggataac    2820
cccaagggaa gttttttcag gcatcgtgtg taagcagaat atataagtgc tgttccctgg    2880
tgcttcctcg ctcactcgag ggcttcgccc tgtcgctcga ctgcggcgag cactactggc    2940
tgtaaaagga cagaccacat catggttctg tgttcattag gttgttctgt ccattgctga    3000
cataatccgc tccacttcaa cgtaacaccg cacgaagatt tctattgttc ctgaaggcat    3060
attcaaatcg ttttcgttac cgcttgcagg catcatgaca gaacactact tcctataaac    3120
gctacacagg ctcctgagat taataatgcg gatctctacg ataatgggag atttttcccga   3180 ctgtttcgtt cgcttctcag tggataacag ccagcttctc tgtttaacag acaaaaacag    3240
catatccact cagttccaca tttccatata aaggccaagg catttattct caggataatt    3300
gtttcagcat cgcaaccgca tcagactccg gcatcgcaaa ctgcacccgg tgccgggcag    3360
ccacatccag cgcaaaaacc ttcgtgtaga cttccgttga actgatggac ttatgtccca    3420
tcaggctttg cagaactttc agcggtatac cggcatacag catgtgcatc gcataggaat    3480
ggcggaacgt atgtggtgtg accggaacag agaacgtcac accgtcagca gcagcggcgg    3540
caaccgcctc cccaatccag gtcctgaccg ttctgtccgt cacttcccag atccgcgctt    3600
tctctgtcct tcctgtgcga cggttacgcc gctccatgag cttatcgcga ataaatacct    3660
gtgacggaag atcacttcgc agaataaata atcctggtg tccctgttga taccgggaag    3720
ccctgggcca acttttggcg aaaatgagac gttgatcggc acgtaagagg ttccaacttt    3780
caccataatg aaataagatc actaccgggc gtattttttg agttatcgag attttcagga    3840
gctaaggaag ctaaaatgga gaaaaaatc actggatata ccaccaccgt tgatatatcc    3900
caatggcatc gtaaagaaca ttttgaggca tttcagtcag ttgctcaatg tacctataac    3960
cagaccgttc agctggatat tacggccttt ttaaagaccg taaagaaaaa taagcacaag    4020
ttttatccgg cctttattca cattcttgcc cgcctgatga atgctcatcc ggaattccgt    4080
atggcaatga aagacggtga gctggtgata tgggatagtg ttcacccttg ttacaccgtt    4140
ttccatgagc aaactgaaac gttttcatcg ctctggagtg aataccacga cgatttccgg    4200
cagtttctac acatatattc gcaagatgtg gcgtgttacg gtgaaaacct ggcctatttc    4260
cctaaagggt ttattgagaa tatgttttc gtctcagcca atccctgggt gagtttcacc    4320
agttttgatt taaacgtggc caatatggac aacttcttcg cccccgtttt caccatgggc    4380
aaatattata cgcaaggcga caaggtgctg atgccgctgg cgattcaggt tcatcatgcc    4440
gtttgtgatg gcttccatgt cggcagaatg cttaatgaat acaacagta ctgcgatgag    4500 tggcagggcg gggcgtaatt ttttttaaggc agttattggt gcccttaaac gcctggttgc    4560
tacgcctgaa taagtgataa taagcggatg aatggcagaa attcgatgat aagctgtcaa    4620
acatgagaat tggtcgacca atacgcaaac cgcctctccc cgcgcgttgg ccgattcatt    4680
aatgcagctg gcacgacagg tttcccgact ggaaagcggg cagtgagcgc aacgcaatta    4740
atgtgagtta gctcactcat taggcacccc aggctttaca ctttatgctc ccggctcgta    4800
tgttgtgtgg aattgtgagc ggataacaat ttcacacagg aaacagctat gaccatgatt    4860
acgccaagcg cgcaattaac cctcactaaa gggaacaaaa gctgggtacc gggcccccc    4920 tcgaggtcga cggtatcgcg attgaagcgt gcgcctgtta ttccaaaaca tacgctcaat    4980
actcaaccgg ttgaagatac ttcgttatcg acaccagctg ccccgatggt ggattcgtta    5040
attgcgcgcg taggagtaat ggctcgcggt aatgccatta ctttgcctgt atgtggtcgg    5100
```

```
gatgtgaagt ttactcttga agtgctccgg ggtgatagtg ttgagaagac ctctcgggta    5160
tggtcaggta atgaacgtga ccaggagctg cttactgagg acgcactgga tgatctcatc    5220 ccttctttc tactgactgg tcaacagaca ccggcgttcg gtcgaagagt atctggtgtc     5280
atagaaattg ccgatgggag tcgccgtcgt aaagctgctg cacttaccga aagtgattat    5340
cgtgttctgg ttggcgagct ggatgatgag cagatggctg cattatccag attgggtaac    5400
gattatcgcc caacaagtgc ttatgaacgt ggtcagcgtt atgcaagccg attgcagaat    5460
gaatttgctg gaaatatttc tgcgctggct gatgcggaaa atatttcacg taagattatt    5520
acccgctgta tcaacaccgc caaattgcct aaatcagttg ttgctctttt ttctcacccc    5580
ggtgaactat ctgcccggtc aggtgatgca cttcaaaaag cctttacaga taaagaggaa    5640
ttacttaagc agcaggcatc taaccttcat gagcagaaaa aagctggggt gatatttgaa    5700
gctgaagaag ttatcactct tttaacttct gtgcttaaaa cgtcatctgc atcaagaact    5760
agtttaagct cacgacatca gtttgctcct ggagcgacag tattgtataa gggcgataaa    5820
atggtgctta acctggacag gtctcgtgtt ccaactgagt gtatagagaa aattgaggcc    5880
attcttaagg aacttgaaaa gccagcaccc tgatgcgacc acgttttagt ctacgtttat    5940
ctgtctttac ttaatgtcct tgttacagg ccagaaagca taactggcct gaatattctc     6000
tctgggccca ctgttccact tgtatcgtcg gtctgataat cagactggga ccacggtccc    6060
actcgtatcg tcggtctgat tattagtctg gaccacggt cccactcgta tcgtcggtct     6120
gattattagt ctgggaccac ggtcccactc gtatcgtcgg tctgataatc agactgggac    6180
cacggtccca ctcgtatcgt cggtctgatt attagtctgg accatggtc ccactcgtat     6240 cgtcggtctg attattagtc tgggaccacg gtcccactcg tatcgtcggt ctgattatta    6300
gtctggaacc acggtcccac tcgtatcgtc ggtctgatta ttagtctggg accacggtcc    6360
cactcgtatc gtcggtctga ttattagtct gggaccacga tcccactcgt tgtcggtc      6420 tgattatcgg tctgggacca cggtcccact tgtattgtcg atcagactat cagcgtgaga    6480
ctacgattcc atcaatgcct gtcaagggca gtattgaca tgtcgtcgta acctgtagaa     6540
cggagtaacc tcggtgtgcg gttgtatgcc tgctgtggat tgctgctgtg tcctgcttat    6600
ccacaacatt ttgcgcacgg ttatgtggac aaaatacctg gttacccagg ccgtgccggc    6660
acgttaaccg ggctgcatcc gatgcaagtg tgtcgctgtc gagtacaggt gttggccgtt    6720
gtgcccggac gggagatcga gtcccgtgat cggatcgcca agatatgcga caattttgct    6780
attagcaaag tagcccggga tatggagcag ttgttggcca ccaaaaattt ggagaagcca    6840
ctggagcagc cggagaatgg gtacacctac aaggccacct ggttcatgca gttccgggcg    6900
gtcctgtggc gatcctggct gtcggtgctc aaggaaccac tcctcgtaaa agtgcgactt    6960
attcagacaa cggtgagtgg ttccagtgga aacaaatgat ataacgctta caattcttgg    7020
aaacaaattc gctagatttt agttagaatt gcctgattcc acacccttct tagtttttt     7080 caatgagatg tatagtttat agttttgcag aaaataaata aatttcattt aactcgcgaa    7140
catgttgaag atatgaatat taatgagatg cgagtaacat tttaatttgc agatggttgc    7200
catcttgatt ggcctcatct tttttgggcca acaactcacg caagtgggcg tgatgaatat   7260
caacggagcc atcttcctct tcctgaccaa catgaccttt caaaacgtct tgccacgat    7320 aaatgtaagt cttgtttaga atacatttgc atattaataa tttactaact ttctaatgaa    7380
tcgatggccg gcctagtctt ctacgtagac ttattgtctt aattaacaat tcggcgcagc    7440
accatggcct gaaataacct ctgaaagagg aacttggtta ggtaccttct gaggcggaaa    7500
```

| | |
|---|---:|
| gaaccagctg tggaatgtgt gtcagttagg gtgtggaaag tccccaggct ccccagcagg | 7560 |
| cagaagtatg caaagcatgc atctcaatta gtcagcaacc aggtgtggaa agtccccagg | 7620 |
| ctccccagca ggcagaagta tgcaaagcat gcatctcaat tagtcagcaa ccatagtccc | 7680 |
| gcccctaact ccgcccatcc cgcccctaac tccgcccagt tccgcccatt ctccgcccca | 7740 |
| tggctgacta atttttttat ttatgcagag gccgaggccg cctcggcctc tgagctattc | 7800 |
| cagaagtagt gaggaggctt ttttggaggc ctaggatcga tccaccggtc gccaccatgg | 7860 |
| tgagcaaggg cgaggagctg ttcaccgggg tggtgcccat cctggtcgag ctggacggcg | 7920 |
| acgtaaacgg ccacaagttc agcgtgtccg gcgagggcga gggcgatgcc acctacggca | 7980 |
| agctgaccct gaagttcatc tgcaccaccg gcaagctgcc cgtgccctgg cccaccctcg | 8040 |
| tgaccaccct gacctacggc gtgcagtgct tcagccgcta ccccgaccac atgaagcagc | 8100 |
| acgacttctt caagtccgcc atgcccgaag ctacgtcca ggagcgcacc atcttcttca | 8160 |
| aggacgacgg caactacaag acccgcgccg aggtgaagtt cgaggcgac accctggtga | 8220 |
| accgcatcga gctgaagggc atcgacttca aggaggacgg caacatcctg ggcacaagc | 8280 |
| tggagtacaa ctacaacagc cacaacgtct atatcatggc cgacaagcag aagaacggca | 8340 |
| tcaaggtgaa cttcaagatc cgccacaaca tcgaggacgg cagcgtgcag ctcgccgacc | 8400 |
| actaccagca gaacaccccc atcggcgacg gccccgtgct gctgcccgac aaccactacc | 8460 |
| tgagcaccca gtccgccctg agcaaagacc ccaacgagaa gcgcgatcac atggtcctgc | 8520 |
| tggagttcgt gaccgccgcc gggatcactc tcggcatgga cgagctgtac aagtaaagcg | 8580 |
| gccgcctgca gcttaagacc ggtaagctag cttacgcgtg ctagcgggcc cgttaacttg | 8640 |
| tttattgcag cttataatgg ttacaaataa agcaatagca tcacaaattt cacaaataaa | 8700 |
| gcatttttt cactgcattc tagttgtggt ttgtccaaac tcatcaatgt atcttatcat | 8760 |
| gtctggatct taattaacca gcatcgcat cgattcgatt taggtgttca cctcagagct | 8820 |
| gccagttttt atgagggagg cccgaagtcg atggcaagtg tagcggtcac gctgcgcgta | 8880 |
| accaccacac ccgccgcgct taatgcgccg ctacagggcg cgtcccattc gccattcagg | 8940 |
| ctgcgcaact gttgggaagg gcgatcggtg cgggcctctt cgctattacg ccagctggcg | 9000 |
| aaagggggat gtgctgcaag gcgattaagt tgggtaacgc cagggttttc ccagtcacga | 9060 |
| cgttgtaaaa cgacggccag tgagcgcgcg taatacgact cactataggg cgaattgag | 9120 |
| ctccaccgcg gtggcggccg ctctagaact agtggatcga tccccgggc tgcaggaatt | 9180 |
| cgatatcaag ctt | 9193 |

<210> SEQ ID NO 60
<211> LENGTH: 5520
<212> TYPE: DNA
<213> ORGANISM: Artificial Sequence
<220> FEATURE:
<223> OTHER INFORMATION: pRK-GFP

<400> SEQUENCE: 60

| | |
|---|---:|
| ttcgagctcg cccgacattg attattgact agttattaat agtaatcaat tacgggtca | 60 |
| ttagttcata gcccatatat ggagttccgc gttacataac ttacggtaaa tggcccgcct | 120 |
| ggctgaccgc ccaacgaccc ccgcccattg acgtcaataa tgacgtatgt tcccatagta | 180 |
| acgccaatag ggactttcca ttgacgtcaa tgggtggagt atttacggta aactgcccac | 240 |
| ttggcagtac atcaagtgta tcatatgcca agtacgcccc ctattgacgt caatgacggt | 300 |

```
aaatggcccg cctggcatta tgcccagtac atgaccttat gggactttcc tacttggcag    360
tacatctacg tattagtcat cgctattacc atggtgatgc ggttttggca gtacatcaat    420
gggcgtggat agcggtttga ctcacgggga tttccaagtc tccaccccat tgacgtcaat    480
gggagtttgt tttggcacca aaatcaacgg gactttccaa aatgtcgtaa caactccgcc    540
ccattgacgc aaatgggcgg taggcgtgta cggtgggagg tctatataag cagagctcgt    600
ttagtgaacc gtcagatcgc ctggagacgc catccacgct gttttgacct ccatagaaga    660
caccgggacc gatccagcct ccgcggccgg aacggtgca ttggaacgcg gattccccgt     720
gccaagagtg acgtaagtac cgcctataga gtctataggc ccaccccctt ggcttcgtta    780
gaacgcggct acaattaata cataacctta tgtatcatac acatacgatt taggtgacac    840
tatagaataa catccacttt gcctttctct ccacaggtgt ccactcccag gtccaactgc    900
acctcggttc taagcttgcc gccatggact acaaggacga cgatgacaag gggtcgagcg    960
tcgacgtgag caagggcgag gagctgttca ccggggtggt gcccatcctg gtcgagctgg   1020
acggcgacgt aaacggccac aagttcagcg tgtccggcga gggcgagggc gatgccacct   1080
acggcaagct gaccctgaag ttcatctgca ccaccggcaa gctgcccgtg ccctggccca   1140
ccctcgtgac caccctgacc tacggcgtgc agtgcttcag ccgctacccc gaccacatga   1200
agcagcacga cttcttcaag tccgccatgc ccgaaggcta cgtccaggag cgcaccatct   1260
tcttcaagga cgacggcaac tacaagaccc gcgccgaggt gaagttcgag ggcgacaccc   1320
tggtgaaccg catcgagctg aagggcatcg acttcaagga ggacggcaac atcctggggc   1380
acaagctgga gtacaactac aacagccaca acgtctatat catggccgac aagcagaaga   1440
acggcatcaa ggtgaacttc aagatccgcc acaacatcga ggacggcagc gtgcagctcg   1500
ccgaccacta ccagcagaac acccccatcg gcgacggccc cgtgctgctg cccgacaacc   1560
actacctgag cacccagtcc gccctgagca agacccccaa cgagaagcgc gatcacatgg   1620
tcctgctgga gttcgtgacc gccgccggga tcactctcgg catggacgag ctgtacaagg   1680
cggccgcgac ctgcaggcgc agaactggta ggtatggaag atccctcgag gatccccggg   1740
taccgagctc gaattcatag gtaggtaaat cgatggccgc catggcccaa cttgtttatt   1800
gcagcttata atggttacaa ataaagcaat agcatcacaa atttcacaaa taaagcattt   1860
ttttcactgc attctagttg tggtttgtcc aaactcatca atgtatctta tcatgtctgg   1920
atcgggaatt aattcggcgc agcaccatgg cctgaaataa cctctgaaag aggaacttgg   1980
ttaggtacct tctgaggcgg aaagaaccag ctgtggaatg tgtgtcagtt agggtgtgga   2040
aagtccccag gctccccagc aggcagaagt atgcaaagca tgcatctcaa ttagtcagca   2100
accaggtgtg gaaagtcccc aggctcccca gcaggcagaa gtatgcaaag catgcatctc   2160
aattagtcag caaccatagt cccgccccta actccgccca tcccgcccct aactccgccc   2220
agttccgccc attctccgcc ccatggctga ctaatttttt ttatttatgc agaggccgag   2280
gccgcctcgg cctgtgagct attccagaag tagtgaggag gcttttttgg aggcctaggc   2340
ttttgcaaaa agctgttaac agcttggcac tggccgtcgt tttacaacgt cgtgactggg   2400
aaaaccctgg cgttacccaa cttaatcgcc ttgcagcaca tccccccttc gccacctggc   2460
gtaatagcga agaggcccgc accgatcgcc cttcccaaca gttgcgtagc ctgaatggcg   2520
aatggcgcct gatgcggtat tttctcctta cgcatctgtg cggtatttca caccgcatac   2580
gtcaaagcaa ccatagtacg cgccctgtac gggcgcatta gcgcggcgg gtgtggtggt   2640 tacgcgcagc gtgaccgcta cacttgccag cgccctagcg cccgctcctt tcgctttctt   2700
```

```
cccttccttt ctcgccacgt tcgccggctt tccccgtcaa gctctaaatc gggggctccc    2760
tttagggttc cgatttagtg ctttacggca cctcgacccc aaaaaacttg atttgggtga    2820
tggttcacgt agtgggccat cgccctgata gacggttttt cgccctttga cgttggagtc    2880
cacgttcttt aatagtggac tcttgttcca aactggaaca acactcaacc ctatctcggg    2940
ctattctttt gatttataag ggattttgcc gatttcggcc tattggttaa aaaatgagct    3000
gatttaacaa aaatttaacg cgaattttaa caaaatatta acgtttacaa ttttatggtg    3060
cactctcagt acaatctgct ctgatgccgc atagttaagc caactccgct atcgctacgt    3120
gactgggtca tggctgcgcc ccgacacccg ccaacacccg ctgacgcgcc ctgacgggct    3180
tgtctgctcc cggcatccgc ttacagacaa gctgtgaccg tctccgggag ctgcatgtgt    3240
cagaggtttt caccgtcatc accgaaacgc gcgaggcagt attcttgaag acgaaagggc    3300
ctcgtgatac gcctattttt ataggttaat gtcatgataa taatggtttc ttagacgtca    3360
ggtggcactt ttcggggaaa tgtgcgcgga accctatttg tttattttc taaatacat      3420 tcaaatatgt atccgctcat gagacaataa ccctgataaa tgcttcaata atattgaaaa    3480
aggaagagta tgagtattca acatttccgt gtcgcccctta ttcccttttt tgcggcattt    3540
tgccttcctg ttttgctca cccagaaacg ctggtgaaag taaaagatgc tgaagatcag     3600
ttgggtgcac gagtgggtta catggaactg gatctcaaca gcggtaagat ccttgagagt    3660
tttcgccccg aagaacgttt tccaatgatg agcacttttta aagttctgct atgtggcgcg    3720
gtattatccc gtgatgacgc cgggcaagag caactcggtc gccgcataca ctattctcag    3780
aatgacttgg ttgagtactc accagccaca gaaaagcatc ttacggatgg catgacagta    3840
agagaattat gcagtgctgc cataaccatg agtgataaca ctgcggccaa cttacttctg    3900
acaacgatcg gaggaccgaa ggagctaacc gcttttttgc acaacatggg ggatcatgta    3960
actcgccttg atcgttggga accggagctg aatgaagcca taccaaacga cgagcgtgac    4020
accacgatgc cagcagcaat ggcaacaacg ttgcgcaaac tattaactgg cgaactactt    4080
actctagctt cccggcaaca attaatagac tggatggagg cggataaagt tgcaggacca    4140
cttctgcgct cggcccttcc ggctggctgg tttattgctg ataaatctgg agccggtgag    4200
cgtgggtctc gcggtatcat tgcagcactg gggccagatg gtaagccctc ccgtatcgta    4260
gttatctaca cgacggggag tcaggcaact atggatgaac gaaatagaca gatcgctgag    4320
ataggtgcct cactgattaa gcattggtaa ctgtcagacc aagtttactc atatatactt    4380
tagattgatt taaaacttca ttttaattt aaaaggatct aggtgaagat cctttttgat      4440
aatctcatga ccaaaatccc ttaacgtgag ttttcgttcc actgagcgtc agaccccgta     4500
gaaaagatca aaggatcttc ttgagatcct ttttttctgc gcgtaatctg ctgcttgcaa    4560
acaaaaaaac caccgctacc agcggtggtt tgtttgccgg atcaagagct accaactctt    4620
tttccgaagg taactggctt cagcagagcg cagataccaa atactgtcct tctagtgtag    4680
ccgtagttag gccaccactt caagaactct gtagcaccgc ctacatacct cgctctgcta    4740
atcctgttac cagtggctgc tgccagtggc gataagtcgt gtcttaccgg gttggactca    4800
agacgatagt taccggataa ggcgcagcgg tcgggctgaa cggggggttc gtgcacacag    4860
cccagcttgg agcgaacgac ctacaccgaa ctgagatacc tacagcgtga gcattgagaa    4920
agcgccacgc ttcccgaagg gagaaaggcg gacaggtatc cggtaagcgg cagggtcgga    4980
acaggagagc gcacgaggga gcttccaggg ggaaacgcct ggtatcttta tagtcctgtc    5040
```

```
gggtttcgcc acctctgact tgagcgtcga tttttgtgat gctcgtcagg ggggcggagc    5100
ctatggaaaa acgccagcaa cgcggccttt ttacggttcc tggccttttg gtggcctttt    5160
gctcacatgt tctttcctgc gttatcccct gattctgtgg ataaccgtat taccgccttt    5220
gagtgagctg ataccgctcg ccgcagccga acgaccgagc gcagcgagtc agtgagcgag    5280
gaagcggaag agcgcccaat acgcaaaccg cctctccccg cgcgttggcc gattcattaa    5340
tccagctggc acgacaggtt tcccgactgg aaagcgggca gtgagcgcaa cgcaattaat    5400
gtgagttacc tcactcatta ggcacccag gctttacact ttatgcttcc ggctcgtatg    5460
ttgtgtggaa ttgtgagcgg ataacaattt cacacaggaa acagctatga ccatgattac    5520
```